US012576044B2

(12) United States Patent
Knepper

(10) Patent No.: US 12,576,044 B2
(45) Date of Patent: *Mar. 17, 2026

(54) TREATMENT OF ALZHEIMER'S DISEASE

(71) Applicant: Paul A. Knepper, Chicago, IL (US)

(72) Inventor: Paul A. Knepper, Chicago, IL (US)

( * ) Notice: Subject to any disclaimer, the term of this patent is extended or adjusted under 35 U.S.C. 154(b) by 427 days.

This patent is subject to a terminal disclaimer.

(21) Appl. No.: 18/143,001

(22) Filed: May 3, 2023

(65) Prior Publication Data

US 2023/0270689 A1 Aug. 31, 2023

Related U.S. Application Data

(60) Continuation-in-part of application No. 17/130,405, filed on Dec. 22, 2020, now abandoned, which is a division of application No. 15/752,458, filed as application No. PCT/US2016/047524 on Aug. 18, 2016, now abandoned.

(60) Provisional application No. 62/207,535, filed on Aug. 20, 2015.

(51) Int. Cl.

| | |
|---|---|
| ***A61K 31/05*** | (2006.01) |
| ***A61K 9/48*** | (2006.01) |
| ***A61K 31/352*** | (2006.01) |
| ***A61K 31/485*** | (2006.01) |
| ***A61K 45/06*** | (2006.01) |
| ***A61P 7/02*** | (2006.01) |
| ***A61P 17/02*** | (2006.01) |
| ***A61P 25/28*** | (2006.01) |
| ***A61P 27/06*** | (2006.01) |

(52) U.S. Cl.

CPC ............ *A61K 31/05* (2013.01); *A61K 9/4858* (2013.01); *A61K 31/352* (2013.01); *A61K 31/485* (2013.01); *A61K 45/06* (2013.01); *A61P 7/02* (2018.01); *A61P 17/02* (2018.01); *A61P 25/28* (2018.01); *A61P 27/06* (2018.01)

(58) Field of Classification Search

CPC .... A61K 31/05; A61K 9/4858; A61K 31/352; A61K 31/485; A61K 45/06; A61P 7/02; A61P 27/06; A61P 25/28; A61P 17/02

USPC .......................................................... 514/730

See application file for complete search history.

(56) References Cited

U.S. PATENT DOCUMENTS 11,234,942 B2 * 2/2022 Knepper ............... A61K 31/12

OTHER PUBLICATIONS

Raja et al Current Medicinal Chemistry, 2023, 30, 4032-4047 (Year: 2023).*

* cited by examiner

*Primary Examiner* — Yevgeny Valenrod

(74) *Attorney, Agent, or Firm* — Olson & Cepuritis, Ltd.

(57) ABSTRACT

Neurodegenerative diseases are treated by the co-administration to a subject of an effective amount of a stilbene, a flavonol, and a TLR4/MD2 receptor antagonist. A preferred stilbene is resveratrol, a preferred flavonol is quercetin, and a preferred TLR4/MD2 receptor antagonist is curcumin.

7 Claims, 12 Drawing Sheets

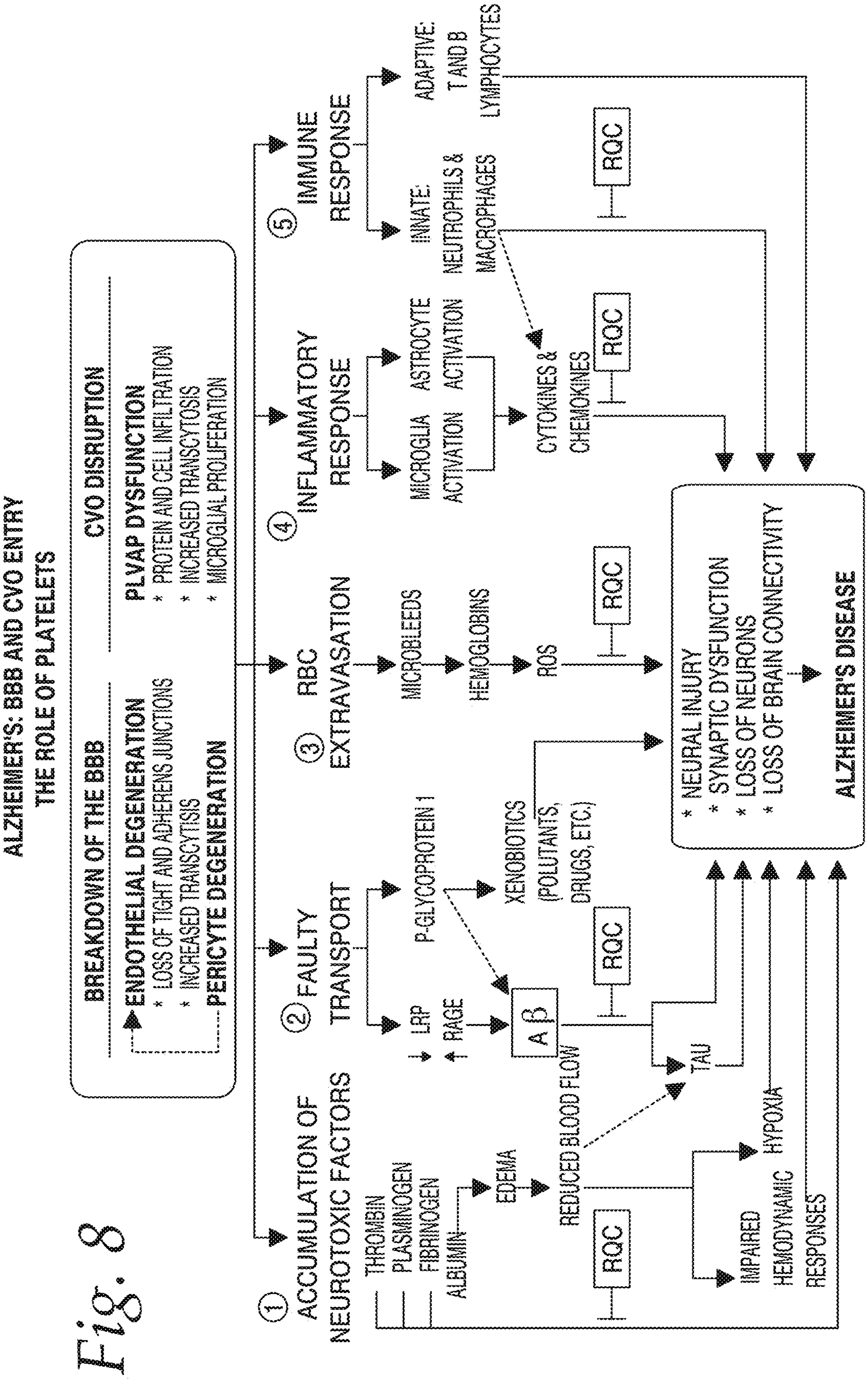

*Fig. 8*

ALZHEIMER'S: BBB AND CVO ENTRY
THE ROLE OF PLATELETS

BREAKDOWN OF THE BBB

ENDOTHELIAL DEGENERATION
* LOSS OF TIGHT AND ADHERENS JUNCTIONS
* INCREASED TRANSGYTISIS
PERICYTE DEGENERATION

CVO DISRUPTION

PLVAP DYSFUNCTION
* PROTEIN AND CELL INFILTRATION
* INCREASED TRANSCYTOSIS
* MICROGLIAL PROLIFERATION

① ACCUMULATION OF NEUROTOXIC FACTORS

THROMBIN
PLASMINOGEN
FIBRINOGEN
ALBUMIN

② FAULTY TRANSPORT

P-GLYCOPROTEIN 1

XENOBIOTICS
(POLUTANTS, DRUGS, ETC.)

LRP
RAGE

A β

RQC

③ RBC EXTRAVASATION

MICROBLEEDS

HEMOGLOBINS

ROS

RQC

④ INFLAMMATORY RESPONSE

MICROGLIA ACTIVATION

ASTROCYTE ACTIVATION

CYTOKINES & CHEMOKINES

RQC

⑤ IMMUNE RESPONSE

INNATE: NEUTROPHILS & MACROPHAGES

ADAPTIVE: T AND B LYMPHOCYTES

RQC

EDEMA

REDUCED BLOOD FLOW

TAU

IMPAIRED HEMODYNAMIC RESPONSES

HYPOXIA

RQC

* NEURAL INJURY
* SYNAPTIC DYSFUNCTION
* LOSS OF NEURONS
* LOSS OF BRAIN CONNECTIVITY

ALZHEIMER'S DISEASE

BEFORE
BASELINE (NO CURCUMIN)

AFTER
POST CURCUMIN

POST MINUS BASELINE WITH
DIFFERENCE SHOWN AS BLACK HIGHLIGHTED

FINAL BINARY IMAGE

OF SPOTS:45
AREA: 9647
RAI: 35.85

TREATMENT OF ALZHEIMER'S DISEASE

CROSS-REFERENCE TO RELATED APPLICATION

This application is a continuation-in-part of U.S. Ser. No. 17/130,405 filed on Dec. 22, 2020 which, in turn, is a division of U.S. Ser. No. 15/752,458, filed on Feb. 13, 2018, now abandoned, which in turn is a U.S. National Phase of PCT/US2016/047524, filed on Aug. 18, 2016 claiming benefit of U.S. Provisional Application Ser. No. 62/207,535, filed on Aug. 20, 2015, each of which is incorporated herein by reference.

FIELD OF INVENTION

This invention relates to therapy of neurodegenerative diseases.

BACKGROUND OF THE INVENTION

Microvascular diseases account for more than one-third of human deaths worldwide. A wide number of microvascular diseases exhibit abnormal platelet functions. Platelets play an important role in arresting of bleeding, i.e., clotting. If platelets do not function as they should, obstructive clotting or serious bleeding can occur.

Platelets (thrombocytes) are fragments of cytoplasm whose primary function is to arrest bleeding. In the blood stream, platelets travel singly, as smooth-surfaced discs. When blood vessels suffer trauma, however, platelets adhere to the exposed subendothelial fibrils, become sticky, and adhere to one another to form a hemostatic plug. The coagulation cascade is illustrated in FIG. 1. Toll-like receptor 4 (TLR4) is a key innate immune receptor in the coagulation cascade, recognizes damage activated molecular patterns, and is important in all microvascular diseases.

A separate and discrete subpopulation of platelets exhibiting enhanced procoagulant (prothrombogenic) activity after stimulation with strong agonists has been identified. See, for example, Mazepa et al., Arterioscler Thromb Vasc Biol 33:1747-1752 (2013). This subpopulation of platelets is referred to as superactivated platelets (SAPs). SAPs are prothrombogenic platelets that are elevated in patients suffering from microvascular diseases such as primary open-angle glaucoma (POAG), a neurodegenerative disease, diabetes, and the like.

Individuals afflicted with such microvascular conditions as Alzheimer's disease, glaucoma, connective tissue disorders, and autoimmune disease benefit from drugs that impact the abnormal platelet function, hemorrhaging, and/or thrombotic events associated with these conditions.

Alzheimer's disease is a systemic microvascular disease and manifests as a degenerative neurological disease. Systemic treatment with a stilbene, a flavonol, and a TLR4/MD2 receptor antagonist is a viable new therapeutic approach to treating Alzheimer's disease and other systemic diseases listed in Table 1, below.

Alzheimer's disease is a progressive neurodegenerative disease and the fifth leading cause of death in the US. Currently, over 6.5 million people in the US have been clinically diagnosed with dementia, of which about 4.5 million cases are estimated to be definitive Alzheimer's disease. Another 6-7 million people in the US have mild cognitive impairment (MCI) that has not been formally diagnosed but likely is associated with early Alzheimer's disease. Taken together, over 10 million people in the US are thought to have some form of Alzheimer's disease.

Still more people are thought to have a preclinical, pre-symptomatic form of Alzheimer's disease that could be identified using biomarkers in the blood, brain, or eyes, although no definitive test has been established. The aggregate cost of care for Alzheimer's disease is expected to be $321 billion in 2022, with about 25%, or $81 billion, paid by patients. The number of people living with Alzheimer's disease is expected to double by 2050 due to a continually growing elderly population and better diagnostic tools for identification.

Etiologically, Alzheimer's disease is a neurodegenerative disease clinically characterized by memory loss and changes in other cognitive abilities. Structurally, the disease is characterized by the accumulation of extracellular beta-amyloid plaques and intracellular neurofibrillary tangles in the brain. Beta-amyloid deposition is widely believed to be the central pathological event in Alzheimer's disease. Change in beta-amyloid is thus the primary structural outcome measure in clinical trials for Alzheimer's disease, whether measured through positron emission tomography (PET) neuroimaging with radiolabel tracers or cerebrospinal fluid (CSF) samples obtained by spinal tab. Historically, the U.S. Food and Drug Administration (FDA) has used change in beta-amyloid as a surrogate outcome measure to evaluate the efficacy of investigational drugs for Alzheimer's disease. Structural surrogate outcome measures may be used when change in the structural outcome correlates to change in the clinical outcome. In certain diseases like Alzheimer's disease, clinical outcomes like cognitive function are difficult to measure in a condensed testing period. Indeed, changes in cognitive function measured by cognitive assessment may take years or even decades to manifest clearly. For this reason, change in beta-amyloid is widely accepted as the primary measure of efficacy in Alzheimer's disease.

TABLE 1

Common Neurodegenerative Diseases: Defining Characteristics

| Disease [1] | Subtype | Prevalence | Defining Pathology |
|---|---|---|---|
| Alzheimer's disease (AD) | Sporadic AD | 6,275,000 | β-amyloid plaques outside neurons and |
| | Hereditary AD | 225,000 | neurofibrillary tau protein tangles inside neurons |
| Vascular | Sporadic VD | 2,200,000 | Atherosclerosis, small vessel disease (SVD), and/or cerebral amyloid angiopathy (CAA) resulting in ischemic, hypoperfusive, or |
| dementia (VD) | Hereditary VD | 20,000 | hemorrhagic white matter brain lesions |
| Dementia with Lewy bodies | Lewy body dementia | 1,400,000 | Alpha-synuclein Lewy bodies in cortical neurons |
| | Parkinson's disease | 1,000,000 | Alpha-synuclein Lewy bodies in the substantia nigra |

[1] Up to 50% of all dementia cases are mixed

In the last decade, increasing evidence has shown that beta-amyloid pathology is not limited to the brain but extends to both the eye and to the systemic vasculature, creating opportunities for the development of new therapeutic targets and biomarkers. As part of the central nervous system, the eye contains many of the same cell types and undergoes many of the same physiological and pathophysiological processes as the brain. It has long been evident that manifestations of Alzheimer's disease can be seen in the eye. In fact, ophthalmologic studies of Alzheimer's disease have found significant ocular changes associated with the disease including retinal ganglion cell and optic nerve degeneration, retinal nerve fiber layer thinning, macular atrophy, reduced blood flow, and narrowed vessel diameter. More recently, it was discovered that beta-amyloid deposits are present in retinal central nervous system (CNS) tissue in Alzheimer's disease. This finding was confirmed in numerous histological studies examining postmortem eyes from Alzheimer's disease patients and from transgenic animal models of the disease.

Currently, it has become possible to quantitate retinal β-amyloid in vivo in living subjects using fundus autofluorescence (FAF) photography with blue light autofluorescence and curcumin as a contrast agent. Curcumin has intrinsic fluorescence properties and binds to beta-amyloid fibrils and oligomers with high affinity and specificity. The ability to track beta-amyloid in retinal CNS tissue in living patients creates opportunities for clinical trials for Alzheimer's disease to use retinal beta-amyloid as a surrogate endpoint. This method is significantly more accessible and without the dangers of methods currently used to identify beta-amyloid in clinical trials including PET-radiolabel imaging and CSF samples obtained by spinal tap. Since 2017, at least 6 studies have been published reporting the successful detection of retinal beta-amyloid in vivo using FAF imaging using curcumin as a marker. The FAF-curcumin method is routinely able to identify retinal beta-amyloid in patients with Alzheimer's disease and to distinguish Alzheimer's disease from other types of dementia. Importantly, while retinal beta-amyloid may be present even in healthy individuals or those with other types of dementia or degenerative disease, the characteristically high levels in Alzheimer's disease distinguish it from normal aging or other conditions. Retinal beta-amyloid may be present before any cognitive clinical symptoms manifest and thus could be a useful clinical test for identifying possible Alzheimer's disease well before conventional existing methods. Moreover, early-developing retinal beta-amyloid can serve as a novel outcome measure to evaluate the efficacy of both preventative and therapeutic treatments for the disease. At least one clinical trial has used retinal beta-amyloid as a primary outcome measure for Alzheimer's disease. Although this study did not use curcumin as a contrast agent, it did show that retinal beta-amyloid is a viable structural endpoint in clinical trials and correlates well with changes in brain beta-amyloid.

SUMMARY OF INVENTION

Neurodegenerative diseases are treated by the co-administration to a subject of an effective amount of a stilbene, a flavonol, and a TLR4/MD2 receptor antagonist. A preferred stilbene is resveratrol (R), a preferred flavonol is quercetin (Q), and a preferred TLR4/MD2 receptor antagonist is curcumin (C). To a subject in need of Alzheimer's disease treatment, preferably about 2 milligrams to about 10,000 milligrams of resveratrol, about 2.4 milligrams to about 12,000 milligrams of quercetin, and about 2 milligrams to about 10,000 milligrams of curcumin are administrated daily.

BRIEF DESCRIPTION OF DRAWINGS

In the drawings,

In FIGS. 2A-2C arrows identify locations of hemorrhages within the capillary bed.

FIG. 8 shows the breakdown of the blood-brain barrier (BBB) and disruption of the circumventricular organs (CVOs) in Alzheimer's disease and the role of platelets. (1) BBB and CVO permeability leads to the entry and accumulation of blood- and platelet-derived neurotoxic factors such as thrombin, fibrinogen, plasminogen, and albumin. These factors can cause reduced blood flow and hypoxia, which can lead to neuron cell death. Platelets may also facilitate the entry of neurotoxic beta-amyloid and tau proteins which are hallmarks of Alzheimer's disease pathology. (2) Faulty transport mechanisms are a consequence of BBB and CVO breakdown that directly contribute to the entry of neurotoxic factors into the brain. Faulty transport also contributes to impaired clearance (and thus accumulation) of toxic materials. Altered expression levels of transport proteins lipoprotein receptor-related protein 1 (LRP1), receptor for advanced glycation end products (RAGE), and p-glycoprotein 1 are known to induce accumulation of beta-amyloid and xenobiotic materials such as environmental pollutants, hydrocarbons, and pharmaceutical drugs which can lead to neuron cell injury and death. (3) BBB and CVO breakdown leads to the loss of structural integrity in brain capillaries resulting in hemorrhages, microbleeds, and oxidative stress through the production of harmful reactive oxygen species (ROS). This is evident in nailfold capillary studies showing a loss of structural integrity and increase in nailfold hemorrhages in Alzheimer's disease. (4) The accumulation of toxic blood-derived materials in the brain induces a chronic neuroinflammatory response through the continued activation of microglia and astrocytes. This process occurs through immune receptors such as Toll-like receptor 4 (TLR4) and results in the production of cytokines and chemokines that can lead to neuron cell injury and death. Neuroinflammation further exacerbates beta-amyloid toxicity by promoting aggregation and increasing metabolism of the more toxic species. (5) The innate and adaptive immune systems respond to the accumulation of toxic materials in the brain through the activation of neutrophils, macrophages, and lymphocytes. Like microglia and astrocytes, activation of these immune cells leads to chronic neuroinflammation and, in some cases, the production of autoantibodies.

DESCRIPTION OF PREFERRED EMBODIMENTS

Superactivated platelets (SAPs) are prothrombogenic and are prevalent in afflictions and diseases that have microvascular components, such as primary open-angle glaucoma (POAG) and neurodegenerative diseases such as dementia, Alzheimer's disease, transient ischemic attacks, ischemic stroke, and the like. SAPs also negatively influence recruitment of endothelial progenitor cells (EPCs) and repair of damaged blood vessel endothelium, and are responsible for increased number of nailfold hemorrhages and hemorrhages at the optic disc in patients suffering from POAG.

It has now been found that the SAP population in a subject can be reduced by a combinatorial drug intervention strategy and provide treatment for microvascular diseases such as POAG, neurodegenerative diseases, such as Alzheimer's disease, scar formation, thromboembolic diseases, and the like.

Alzheimer's disease is primarily characterized by toxic beta-amyloid plaques in the brain. The aggregation and accumulation of these plaques is widely considered to be the central pathological event in the progression of the disease. Although most therapies evaluated for Alzheimer's disease target aggregation of beta-amyloid into insoluble plaques, there are in fact numerous opportunities for intervention associated with beta-amyloid toxicity from the initial cause of accumulation to the immune-driven response. These mechanisms, diagramed in FIG. 8, can be broadly grouped into 5 primary pathways: 1) the accumulation and aggregation of neurotoxic material, 2) faulty transport mechanisms, 3) vascular damage and hemorrhaging, 4) the inflammatory response, and 5) the immune response. In contrast to immunotherapy-based treatments, the present treatment that targets multiple points along the pathway leading to the development and progression of Alzheimer's disease.

Barriers in the Brain: The Blood-Brain Barrier and Circumventricular Organs in Alzheimer's Disease Elevated levels of beta-amyloid in Alzheimer's disease can be caused by multiple mechanisms including impaired barrier function and impaired influx and efflux pathways. The primary barriers in the brain are the blood-brain barrier (BBB) and circumventricular organs (CVOs). The BBB and CVOs represent the two pathways for toxic proteins to enter or exit the brain. Breakdown or disruption of these structures facilitates the entry or accumulation of blood-derived toxins such as beta-amyloid and is implicated in Alzheimer's disease and other cognitive disorders. On a cellular level, the regulation of beta-amyloid levels in the brain depends on influx and efflux pathways regulated by the receptor for advanced glycation end products (RAGE), low-density lipoprotein receptor-related protein 1 (LRP1), and P-glycoprotein (ABCB1).

Figure 1:
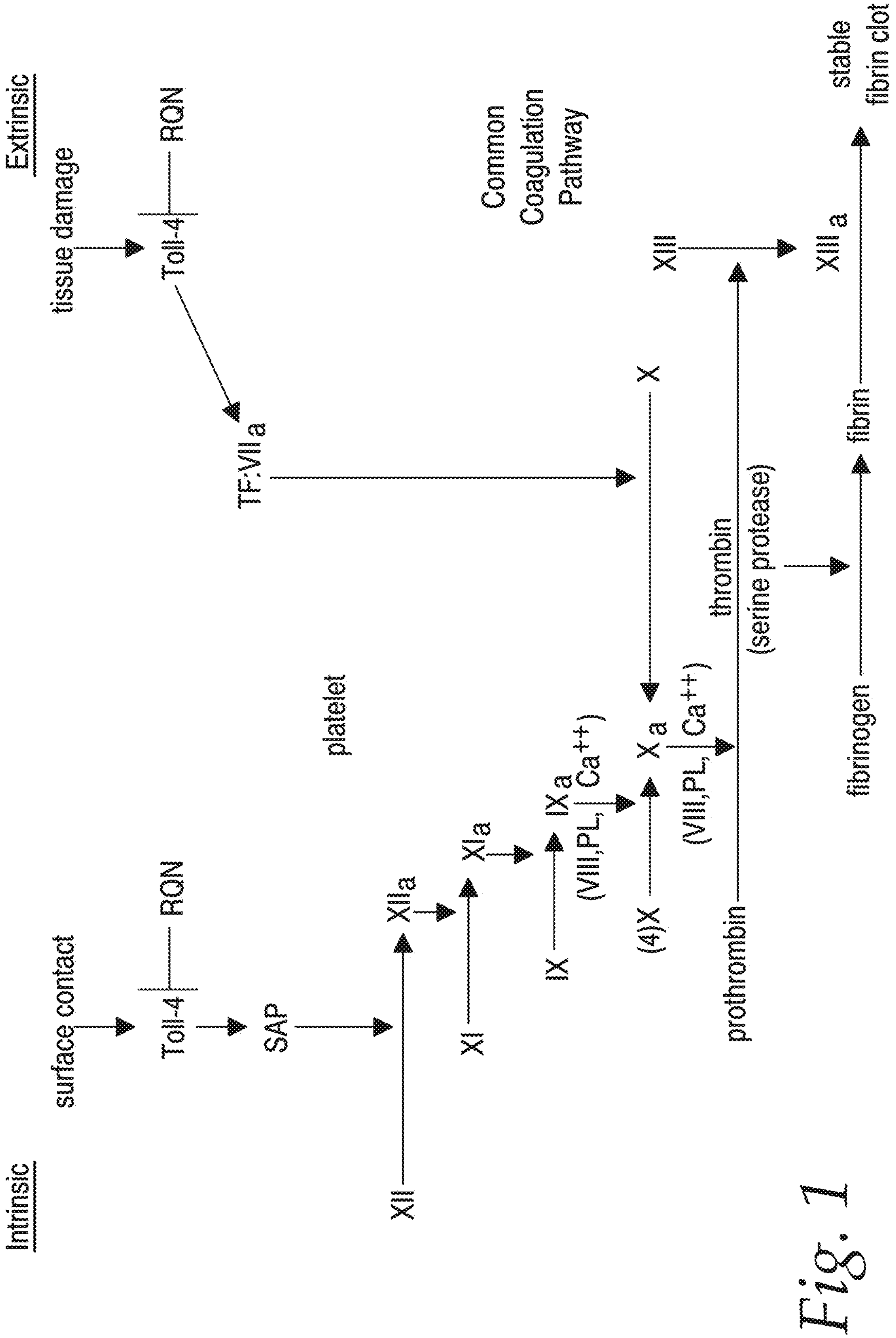
FIG. 1 is a diagram of coagulation cascade showing the intrinsic coagulation pathway (microvascular injury) and the extrinsic coagulation pathway (microvascular tissue damage). RQN denotes combinatorial drug treatment with resveratrol (R), quercetin (Q) and naltrexone (N); Toll-4 denotes toll-like receptor 4; SAP denotes superactivated platelet; XII denotes Hageman factor; XI denotes plasma thromboplastin antecedent (PTA); IX denotes plasma thromboplastin component (PTC); X denotes Stuart-Prower factor; VIII denotes antihemophilic factor (AHF); PL denotes plasma membrane phospholipid; $Ca^{++}$ denotes calcium ions; TF denotes tissue factor; VII denotes Proconvertin; and XIII denotes fibrin-stabilizing factor (FSF). For VII and X-XIII the subscript "a" indicates activated form of factor.
Figure 2A:
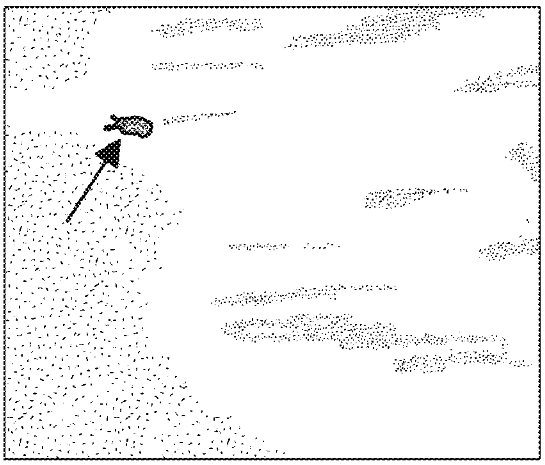
FIG. 2A is a nailfold capillaroscopy image from a 68 year old male suffering from normal tension glaucoma (NTG).
Figure 2B:
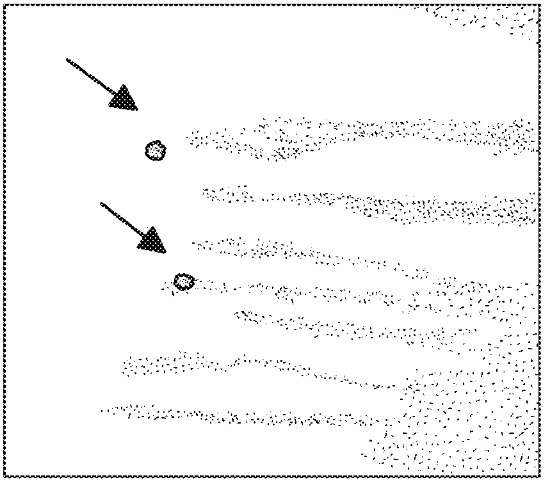
FIG. 2B is a nailfold capillaroscopy image from a 74 year old female suffering from primary open angle glaucoma (POAG).
Figure 2C:
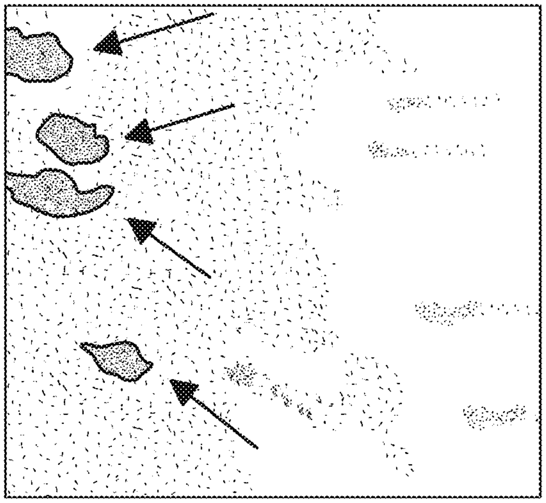
FIG. 2C is a nailfold capillaroscopy image from a 63 year old male suffering from normal tension glaucoma (NTG).
Figure 3:
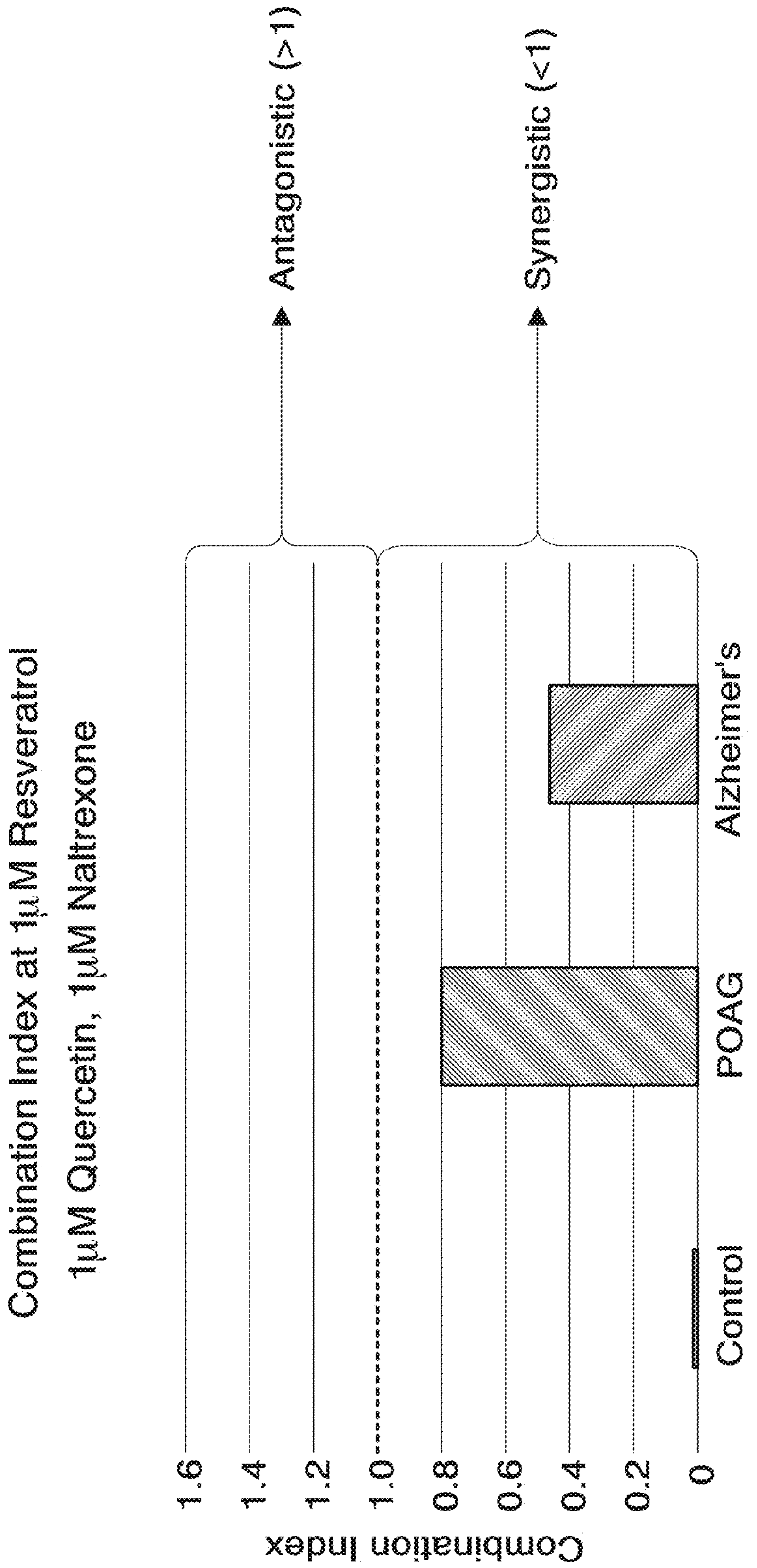
FIG. 3 is a graphical representation of the Combination Index in POAG and Alzheimer's disease patients who have received a combination of resveratrol, quercetin and naltrexone, each at 1 μM concentration.
Figure 4:
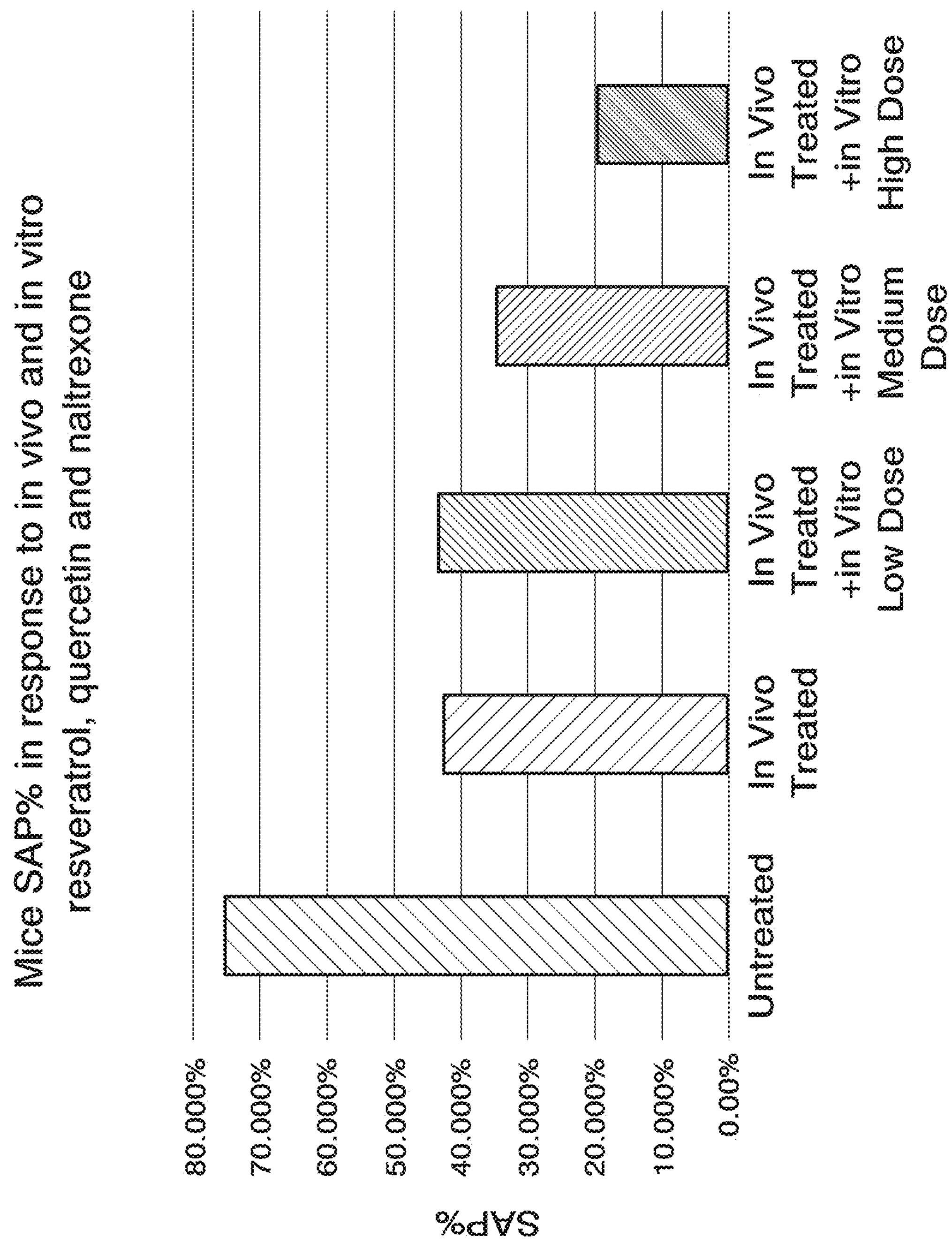
FIG. 4 is a histogram showing the effect of combined in vivo administration of resveratrol, quercetin and naltrexone to mice.
Figure 5:
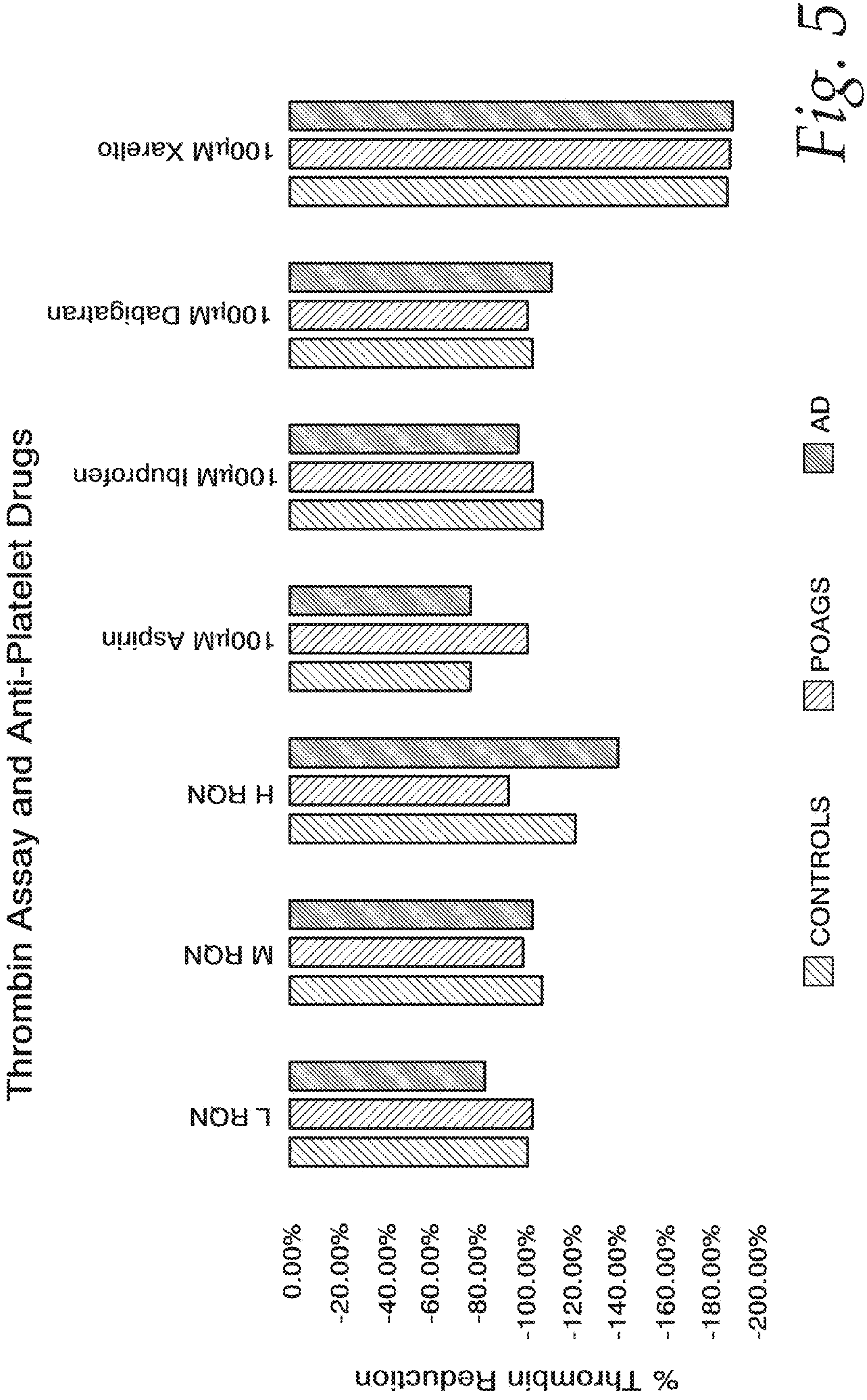
FIG. 5 is a histogram showing the results of a thrombin generation test in POAG patients and Alzheimer's disease patients.
Figure 6:
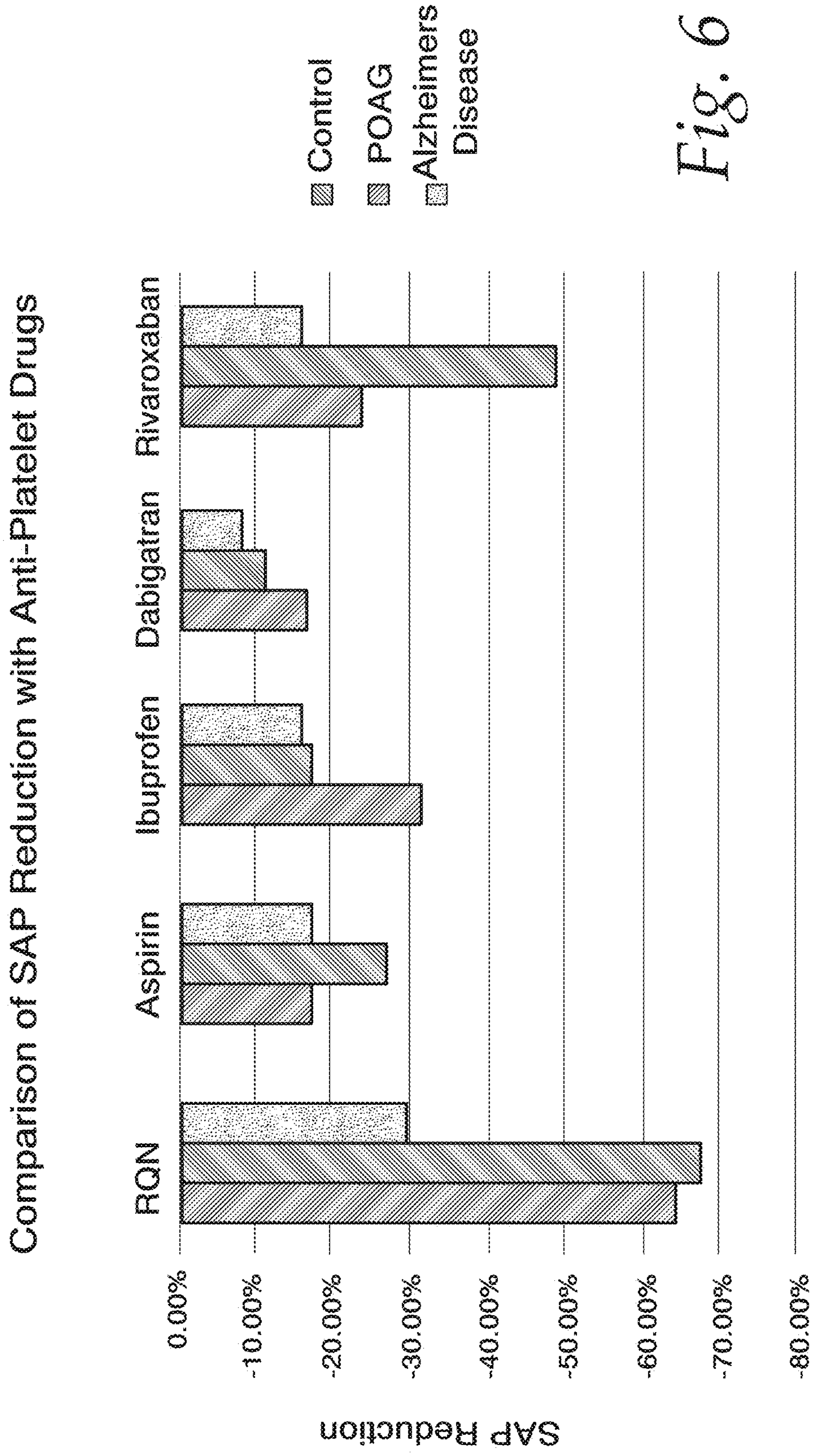
FIG. 6 is a histogram presenting the results of an evaluation of resveratrol, quercetin and naltrexone efficacy in reducing SAPs as compared to known anti-platelet drugs.
Figure 7:
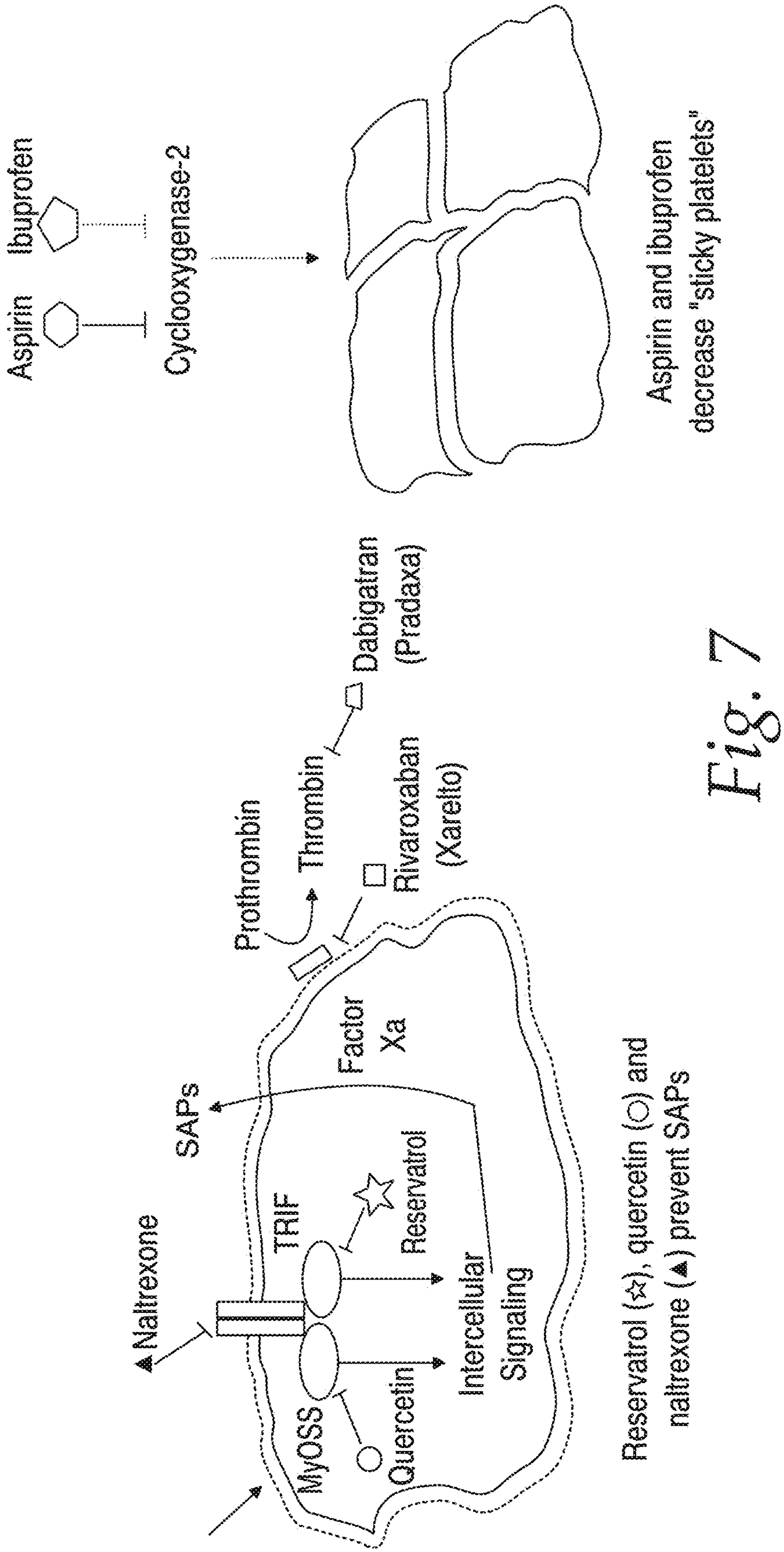
FIG. 7 is a schematic illustration of targets and signaling pathways of resveratrol, quercetin, naltrexone, and known anti-platelet drugs.
Figure 9:
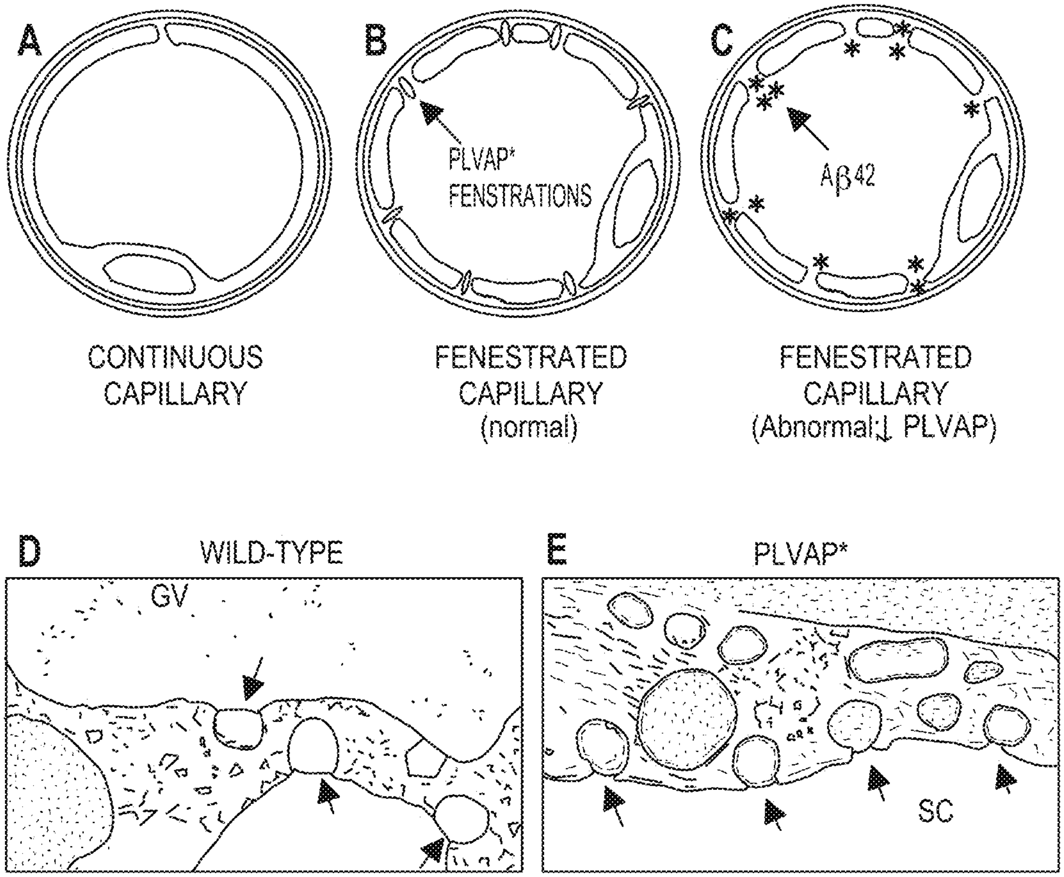
FIG. 9 shows a diagram of (A) continuous capillaries, (B) normal fenestrated capillaries, and (C) abnormal fenestrated capillaries with defective plasmalemma vesicle-associated protein 1 (PLVAP) and containing toxic beta-amyloid (Aβ42) aggregates such as those found in Alzheimer's disease. The electron microscopy images show (D) normal PLVAP-positive fenestrated capillaries surrounding a giant vacuole (GV) and (E) abnormal fenestrated capillaries lacking PLVAP in the endothelium of Schlemm's canal (SC). Fenestrations are denoted by black arrows. Under normal conditions, PLVAP forms a diaphragm that creates a bridge over the opening of the caveolae (D, thin black lines). When PLVAP is reduced or absent, caveolae remain defective and allow for the free exchange of material between blood and tissue.

Alzheimer's disease may be initiated via a vascular mechanism through the accumulation of beta-amyloid in the brain due to impaired barrier function. The BBB is a tightly regulated, highly selective endothelial barrier which only allows certain substances to move into and out of the brain. A compromised BBB can lead to the entry and accumulation of toxic material such as beta-amyloid. The CVOs may act as another point of entry for toxic material into the brain and differ from the BBB in structure, cell population and permeability. CVOs are specialized regions of the brain surrounding the CNS ventricles (CSF-filled chambers in the brain) that lack the continuous endothelium of the BBB and instead contain endothelial fenestrations enabling the exchange of information between the systemic circulation, the CSF, and the brain. Endothelial fenestrations are selectively permeable pores 30-80 nm in diameter and are structurally formed by plasmalemma vesicle-associated protein 1 (PLVAP; FIG. 9). Substances with molecular weights under 10,000 are able to pass through fenestrations, suggesting that various toxic proteins such as beta-amyloid (molecular weight 4,514) can enter the brain at these locations. Accumulation of beta-amyloid due to CVO-based entry could play a role in the vascular onset of Alzheimer's disease.

Blood-derived molecules with molecular weights>10,000 cannot pass freely through fenestrated capillaries but are permeable to the inner basement membrane of the CVOs. As a result, these potentially toxic substances accumulate between the inner and outer basement membranes. For example, the blood-derived protein albumin is known to accumulate in the brain parenchyma through this mechanism and can be a direct cause of cytotoxicity.

The receptor-based influx of beta-amyloid from the blood into the brain interstitial fluid (ISF) is mediated by RAGE. In Alzheimer's disease, RAGE expression is increased in neurons, microglia, and in the microvasculature. The increase in RAGE is associated with elevated beta-amyloid levels in the brain and corresponding cognitive impairment. In contrast, efflux of beta-amyloid from the brain into the blood occurs through several mechanisms including receptor-mediated transport across the BBB and the CSF-ISF drainage pathway through perivascular basement membranes. Receptor-mediated efflux of beta-amyloid is regulated primarily by LRP1 on the abluminal side and ABCB1 on the luminal side. In Alzheimer's disease, decreased expression levels of LRP1 and ABCB1 are associated with elevated beta-amyloid levels in the brain. Once in the blood, beta-amyloid is sequestered by the soluble form of LRP1 (sLRP1) or apolipoprotein (APOE). sLRP1 is responsible for the sequestration of 70-90% of plasma beta-amyloid. Sequestered plasma beta-amyloid is cleared systemically through the liver and/or kidney.

The pathophysiological mechanisms associated with Alzheimer's disease can take years to manifest, resulting in a slow and insidious disease progression. Fortunately, the early identification of these mechanisms is increasingly possible up to 10-20 years before cognitive function is measurably impaired. Thus, early identification of the disease combined with the development of a successful treatment could lead to the prevention of Alzheimer's disease. The present three-drug synergistic combination of resveratrol, quercetin, and curcumin (RQC) is well-suited to address the specific pathological findings in Alzheimer's including neuroinflammation, impaired hemodynamics, oxidative stress, and the accumulation and aggregation of toxic beta-amyloid.

Beta-amyloid can also be transformed into toxic aggregates without altering the overall amount of protein. This mechanism involves the interaction between beta-amyloid fibrils and xenobiotic compounds such as prescription drugs and pollutants facilitated by the chaperone protein lipocalin-type prostaglandin D synthase (L-PGDS). L-PGDS, abundant in the CSF and in peripheral tissues including the lungs and gastrointestinal system, has a strong affinity for lipophilic compounds and enables their diffusion into the brain. Importantly, L-PGDS also binds beta-amyloid fibrils and monomers with high affinity and is known to de-aggregate existing beta-amyloid fibrils and prevent the aggregation of monomers. Under normal physiological conditions, L-PGDS has a neuroprotective function. In the presence of certain xenobiotics, however, L-PGDS facilitates beta-amyloid aggregation by bringing the protein into contact with certain xenobiotics that alter the morphology of beta-amyloid and facilitate the formation of toxic aggregates. Moreover, some xenobiotics block the L-PGDS-beta-amyloid binding site and thus reduce the ability of L-PGDS to de-aggregate beta-amyloid or block its aggregation. Therefore, the presence of xenobiotics such as pollutants actively increases the toxicity of beta-amyloid in the brain and reduces the neuroprotective function of L-PGDS.

RQC Alters the Aggregation of Beta-Amyloid

The overwhelming majority of clinical trials for Alzheimer's disease are based on the assumption that the accumulation and aggregation of insoluble beta-amyloid plaques in the brain causes the disease. The goal of treatment is therefore to reduce the existing burden of beta-amyloid plaques in the brain and to prevent any future aggregation.

Most commonly, experimental treatments have taken the form of immunotherapy involving monoclonal antibodies (mAbs) directed against the beta-amyloid protein. These antibodies prevent aggregation by binding to beta-amyloid monomers or de-aggregate existing beta-amyloid plaques. Like immunotherapy-based treatments, RQC successfully targets beta-amyloid aggregation. However, RQC offers a significantly improved safety profile with oral treatment and provides the benefit of alternative therapeutic mechanisms including anti-inflammatory and antioxidant properties.

As a treatment for Alzheimer's disease, RQC also targets the beta-amyloid protein and alters its aggregation kinetics (Table 2, below). Specifically, RQC de-aggregates existing beta-amyloid oligomers/fibrils and prevents aggregation by binding to the pre-aggregated monomeric form of the protein. Curcumin, the component of RQC with the strongest amyloid-binding capacity, exhibits an $IC_{50}$ of 0.80 μM for oligomers and 1.00 μM for fibrils. These concentrations are within the range of bioavailable doses of curcumin in humans and in the in vivo range expected using RQC. Curcumin prevents aggregation by interacting with beta-amyloid monomers through hydrophobic forces and hydrogen bonds. Additional interactions include π-π interactions with the aromatic side chains of Phe4, Tyr10, Phe19, and Phe20 and cation-π interactions with the side chains aggregates. Curcumin de-aggregates existing oligomers and fibrils by disrupting the salt bridges formed between Asp1, Asp7, Asp23, Glu3, Glu22, Arg5, Lys16, and Lys28.

In comparison to immunotherapy-based treatments, the use of RQC offers a vastly improved safety profile (Table 2). No serious adverse events are associated with the use of oral RQC. In contrast, Alzheimer's disease immunotherapies evaluated in clinical trials are commonly associated with serious adverse events including most notably amyloid-related imaging abnormalities (ARIA), a serious adverse event. ARIA are abnormalities seen on MRI images of the brain characterized as vasogenic edema (ARIA-E) or microhemorrhages and hemosiderosis (ARIA-H). ARIA-E represents an increase in extracellular fluid related to increased permeability of the neurovascular endothelium (BBB) and is frequently symptomatic. ARIA-H is a small lesion corresponding to leakage of blood into adjacent tissue parenchyma and is not associated with specific symptoms or health risks.

TABLE 2

Comparison of Mechanisms and Properties between RQC and Anti-Beta-Amyloid Monoclonal Antibodies Evaluated in Clinical Trials for Alzheimer's disease

| | Mechanism/Property | RQC | Monoclonal Antibodies |
|---|---|---|---|
| Mechanisms | Beta-amyloid aggregation | + | + |
| | Faulty transport | + | −No effect |
| | RBC extravasation > ROS | + | −No effect |
| | Glial cell inflammatory response | + | −No effect |
| | Immune cell response | + | −No effect |
| Properties | Toxicity (adverse events) | No toxicity | ARIA-E (~30%) |
| | Route of administration | Oral | Subcutaneous injection |
| | Duration of treatment effect | Years-Decades | Unknown |

+ indicates an inhibitory effect.

ARIA-E are abnormalities seen on MRI images of the brain that represent an increase in extracellular fluid related to increased permeability of the blood-brain barrier.

ARIA-E, amyloid-related imaging abnormalities-edema/effusion;

RBC, red blood cell;

ROS, reactive oxygen species.

The examples presented herein demonstrate that 1) RQC reduces pathological extravasation in the nailfold capillary bed in patients with Alzheimer's disease; 2) RQC synergistically inhibits the formation of procoagulant "superactivated" platelets, which are increased in Alzheimer's disease and associated with increased thrombin generation and capillary extravasation; 3) RQC binds to beta-amyloid and can function as a fluorescent label for the identification and quantification of beta-amyloid aggregates in the retinas of living patients with pre-clinical-to-advanced Alzheimer's disease; and 4) RQC functions to de-aggregate existing beta-amyloid aggregates and prevent the formation of new aggregates in the blood, eyes, and brains of patients with Alzheimer's disease.

Unless defined otherwise, all technical and scientific terms used herein have the same meaning as is commonly understood by one skilled in the art to which this invention belongs.

As used herein and in the claims, the singular form "a," "an," and "the" includes plural references unless the context clearly dictates otherwise.

The terms "treatment," or "treating" or "ameliorating" as used in the specification and claims refer to an approach for achieving beneficial or desired results, including but not limited to a therapeutic benefit and/or a prophylactic benefit.

The term "therapeutic benefit" as used in the specification and the claims means eradication or amelioration of the underlying disorder being treated. A therapeutic benefit is achieved with the eradication or amelioration of one or more of the physiological symptoms associated with the underlying disorder such that an improvement is observed in the subject, notwithstanding that the subject may still be afflicted with the underlying disorder. For prophylactic benefit, the present compositions may be administered to a subject at risk of developing a particular affliction or disease, or to a subject reporting one or more of the physiological symptoms of a disease even though a diagnosis of the disease may not have been made.

The term "antagonist" as used in the specification and claims refers to a compound having the ability to inhibit a biological function of a target protein or receptor. Accordingly, the term "antagonist" is defined in the context of the biological role of the target protein or receptor.

The term "effective amount" or "therapeutically effective amount" refers to that amount of composition described herein that is sufficient to achieve the intended effect. The effective amount may vary depending upon the intended application or the subject and disease condition being treated, e.g., the weight and age of the subject, the severity of the disease condition, the manner of administration and the like, which can be determined readily by one skilled in the art. This term also applies to a dose that induces a particular response, e.g., reduction of platelet adhesion. The specific dose may vary depending on the particular compounds that constitute the composition, the dosing regimen to be followed, timing of administration, and the physical delivery system in which the composition is carried.

The "effective amount" or "therapeutically effective amount" may be determined by using methods known in the art such as the NFkB-Luciferase Reporter Mice Assay, the Enzyme-Linked Immunosorbent Assay (ELISA), and the like. An increase in circulating IL-6 is indicative of enhanced TLR4 expression by the platelets, thus monitoring of serum IL-6 levels can also be utilized to arrive at an effective amount of the present compositions to be administered to a particular patient.

The "effective amount" or "therapeutically effective amount" also may be determined by using methods known in the art such as the in vitro flow cytometry assay to evaluate the effectiveness of multiple RQC combinations on platelet activation. All possible combinations of pre-defined "low", "medium", and "high" doses of R, Q, and C, respectively, are tested to determine the optimal dose combination. This method can be used to determine optimal dose ranges for a group of patients by identifying the most effective dose combination on average or can be used to determine optimal dose ranges for individual patients by identifying the most effective dose combination in that patient. Pre-defined dose levels are as follows: "low dose" equates to 1 μm R, 1 μm Q, and 0.01 μm C; "medium dose" equates to 5 μm R, 5 μm Q, and 0.1 μm C; "high dose" equates to 10 μm R, 10 μm Q, and 1 μm C.

The stilbene, the flavonol, and the TLR4/MD2 receptor antagonist preferably are present in the composition as a synergistic combination. The description and composition of each preferred component is shown in Table 3, below.

"Subject" refers to an animal, such as a mammal, for example a human.

The term "unit dosage form" as used in the specification and claims refers to physically discrete units suitable as unitary dosages for human subjects and animals, each unit containing a predetermined quantity of active material calculated to produce the desired therapeutic effect in association with the required pharmaceutical diluent, carrier, or vehicle. The specifications for the novel unit dosage forms of this invention are dictated by and directly dependent on (a) the unique characteristics of the active material and the particular therapeutic effect to be achieved, and (b) the limitations inherent in the art of compounding such active material for therapeutic use in humans and animals, as disclosed in detail in the specification, these being features of the present invention. Examples of suitable unit dosage forms in accord with this invention are tablets, capsules, pills, powder packets, granules, wafers, sachets, suppositories, segregated multiples of any of the foregoing, and other forms as herein described.

The designation "μM," as used herein, denotes the micromolar concentration ($10^{-6}$ mol/L) of the indicated compound, e.g., the stilbene, the flavonol, the TLR4/MD2, or the like, available for contact with platelets.

The active ingredients used in the present treatment are a stilbene or any of its biologically active derivatives or metabolites, a flavonol or any of its biologically active derivatives or metabolites, and a TLR4/MD2 receptor antagonist or any of its biologically active derivatives or metabolites inhibit aggregation of superactivated platelets. The stilbene, the flavonol, and the TLR4/MD2 receptor antagonist preferably are administered orally.

Also suitable biologically active derivatives of the foregoing are the covalently binding fluorosulfonyl ($FO_2S$—) and fluorosulfonyloxy ($FO_2SO$—) derivatives of the stilbene, the flavonol, or the TLR4/MD2 receptor antagonist.

TABLE 3

Chemical Information Overview of Resveratrol, Quercetin, and Curcumin

| | Resveratrol | Quercetin | Curcumin |
|---|---|---|---|
| Names/Synonyms | 5-[(E)-2-(4-hydroxyphenyl)ethenyl] benzene-1,3-diol | 2-(3,4-dihydroxyphenyl)-3,5,7-trihydroxychromen-4-one; dihydrate | (1E,6E)-1,7-bis(4-Hydroxy-3-methoxyphenyl)-1,6-heptadiene-3,5-dione |
| | Trans-resveratrol | Quercetin dihydrate | Diferuloylmethane |
| | 3,4',5-Stilbenetriol | Sophoretin | C.I. 75300 |
| | Trans-3,5,4'-Trihydroxystilbene | Meletin | Natural Yellow 3 |
| Structural Formula | $C_{14}H_{12}O_3$ | $C_{15}H_{10}O_7$ (+$2H_2O$) | $C_{21}H_{20}O_6$ |
| Chemical Class | Stilbenoid | Flavonoid | Diarylheptanoid |
| Pharmacological Class(es) | Antioxidant, platelet aggregation inhibitor, enzyme inhibitor | Antioxidant | Non-steroidal anti-inflammatory, antioxidant, antineoplastic, enzyme inhibitor |
| CAS Number | 501-36-0 | 117-39-5 (6151-25-3) | 458-37-7 |
| Source | Japanese knotweed (root) and grape (fruit) | Synthetic | Turmeric (root) |
| Formulation | Trans-resveratrol | Quercetin dihydrate | Turmeric extract standardized to 95% curcuminoids |

The term "pharmaceutically acceptable excipient" as used in the specification and claims includes any and all solvents, dispersion media, coatings, antibacterial and antifungal agents, isotonic and absorption retarding agents, and the like. The use of such agents and media for pharmaceutically-active substances is well known in the art. Supplementary active ingredients can also be incorporated into the compositions described herein.

Such derivatives can be prepared as described in Dong et al., Angew. Chem. Int. Ed., 2014; 53: 9430-9448, and can serve by targeting active serine, tyrosine, threonine, lysine, cysteine or histidine residues.

Suitable stilbenes for the present compositions are resveratrol (3,5,4'-trihydroxy-trans-stilbene), α,β-dihydroresveratrol (3,4',5-trihydroxybibenzyl), pterostilbene (3',5'-dimethoxy resveratrol), pinosylvin (3',5-dihydroxy-transstilbene), piceatannol (3,5,3',4'-tetrahydroxy-trans-stilbene), and the like. Preferred stilbene is resveratrol (R).

Illustrative covalently binding biologically active derivatives of stilbenes are 3,5-dihydroxy-4-fluorosulfonyl-trans-stilbene, 3,5-dihydroxy-4-fluorosulfonyloxy-trans-stilbene, 3,4'-dihydroxy-5-fluorosulfonyl-trans-stilbene, 3,4'-dihydroxy-5-fluorosulfonyloxy-trans-stilbene, and the like.

Suitable flavonols are quercetin (3,3',4'5,7-pentahydroxy-2-phenylchromen-4-one), 3-hydroxyflavone, azaleatin, fisetin, galangin, gossypetin, kaempferide, kaempferol, isorhamnetin, morin, myricetin, natsudaidain, pachypodol, zhamnazin, zhamnetin, and the like. Preferred flavonol is quercetin (Q).

Illustrative covalently binding biologically active derivatives of flavonols are 3,4',5,7-tetrahydroxy-3'-fluorosulfonyl-2-phenylchromen-4-one, 3,4',5,7-tetrahydroxy-3'-fluorosulfonyloxy-2-phenylchromen-4-one, and the like.

Suitable TLR4/MD2 receptor antagonists are naltrexone (N) and curcumin compounds such as curcumin (C) and its biologically active analogs.

Suitable biologically active curcumin analogs are compounds represented by Formula I below, $Ar^1$-L-$Ar^2$ I wherein $Ar^1$ is a phenyl group or a substituted phenyl group represented by Formula II:

II

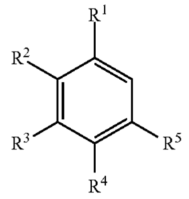

$Ar^2$ is a phenyl group represented by Formula III:

III

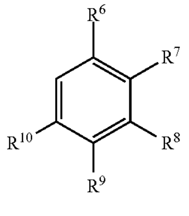

and L is a divalent linking group.

In Formulas II and III each of $R^1$ through $R^{10}$ is independently hydrogen, hydroxyl, methyl, methoxyl, dimethylamine, trifluoromethyl, chloro, fluoro, acetoxyl, cyano, or carboxymethyl.

The divalent linking group L is an alkylene or an alkenylene having 3 to 7 backbone carbon atoms wherein one or more of the backbone carbon atoms is part of a carbonyl or a secondary alcohol. The linking group can be saturated or unsaturated. Preferably, linking group L contains at least one unsaturated carbon-carbon bond.

In a preferred embodiment, L is an alkylene or an alkenylene selected from the group consisting of: —CH═CH—CHO—, —CH═CH—(CO)—CH═CH—, —$CH_2$—$CH_2$—(CO)—$CH_2$—$CH_2$—, —$CH_2$—$CH_2$—CH(OH)—$CH_2$—$CH_2$—,

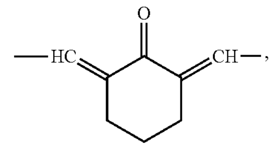, 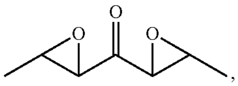,

—CH═CH—(CO)—CR—C(OH)—CH═CH—, —CH═CH—(CO)—$CR_2$—(CO)—CH═CH—, and —CH═CH—(CO)—CH—C(OH)—CH═CH—; R is an alkyl or aryl group including 10 carbon atoms or less.

Illustrative covalently binding biologically active derivatives of TLR4/MD2 receptor antagonists are the fluorosulfate derivatives of curcumin, and the like.

Fluorosulfate derivatives of curcumin can be produced by treating available phenolic OH groups of curcumin with sulfuryl fluoride ($SO_2F_2$) as described in U.S. Pat. No. 10,117,840 to Dong et al.

Preferred TLR4/MD2 receptor antagonist is curcumin.

The active ingredients for the treatment disclosed in the present invention can be administered independently or in such oral dosage forms as tablets, capsules, micelles (each of which can include sustained release or timed release formulations), pills, dermal patches, powders, granules, elixirs, tinctures, suspensions, syrups and emulsions. Likewise, they may also be administered in intravenous (bolus or infusion), intraperitoneal, subcutaneous, or intramuscular form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated and the route of administration; the renal and hepatic function of the patient; and the particular composition employed. An ordinarily skilled physician, veterinarian or clinician can readily determine and prescribe the effective amount of the drug required to prevent, counter or arrest the progress of the condition.

The amount of active ingredients to be administered depends on the age, weight of the patient, the particular condition to be treated, the frequency of administration, and the route of administration.

The daily dose range for the stilbene, such as resveratrol, preferably is about 2 milligrams to about 10,000 milligrams, for the flavonol, such as quercetin, preferably is about 2.4 milligrams to about 12,000 milligrams, and for the TLR4/MD2 receptor antagonist, such as curcumin, preferably is about 2 milligrams to about 10,000 milligrams. The daily dose can be administered as a single dose or in multiple divided doses, preferably 3 or 4 divided doses.

Example 1: Isolation and Cytometry of SAP

A venipuncture sample of 10 mL of blood is obtained from each patient. Of the 10 mL, a 3 mL aliquot of blood is added to a tube containing 0.5 mL of acid-citrate-dextrose solution (38 mM citric acid, 75 mM sodium citrate, 135 mM glucose) to prevent clotting. The aliquot is diluted with 5 mL of buffered saline glucose citrate solution (129 mM NaCl, 13.6 mM sodium citrate, 11.1 mM glucose, 1.6 mM $KH_2PO_4$, 8.6 mM $NaH_2PO_4$, pH 7.3) and centrifuged. After centrifuging at 1100 rpm for 10 minutes at room temperature, platelet rich plasma (PRP), which is the upper layer, is removed. The PRP is transferred to a new tube, leaving about 0.5 mL above the buffy coat layer. The PRP-containing tube is incubated with 10 μL of thrombin and convulxin, two agonists that activate the platelets, for five minutes. Platelets are then treated with biotinylated fibrinogen and stained with the following fluorophores: APC-streptavidin (APC-SA), FITC-PAC1, and PE-anti-CD41. PE-anti-CD41 recognizes the platelet-specific, transmembrane protein CD41. FITC-PAC1 identifies activated platelets by recognizing GPIIaIIIb which increases its expression at the surface upon activation. APC-SA recognizes superactivated platelets that more readily bind the biotinylated fibrinogen to their surface.

All fluorophores are excited at 488 nm by argon laser of the flow cytometer. Their emission spectra are well separated, thereby allowing simultaneous, multi-color immunofluorescence measurements. Table 4, below, describes each fluorophore and the specific cell type it identifies.

TABLE 4

Platelet Fluorochromes

| | | Protein profile | Flurophores to detect |
|---|---|---|---|
| Platelets | Resting | $CD41^+$/SB-Fibrinogen$^-$/PAC1$^-$ | PE-CD41 |
| | Activated | $CD41^+$/SB-Fibrinogen$^-$/PAC1$^+$ | PE-CD41/ FITC-PAC1 |
| | SAPs | $CD41^+$/SB-Fibrinogen$^+$/PAC1$^-$ | PE-CD41/ APC-SA |

Each sample is analyzed by a Beckman Coulter CyAn flow cytometer (Beckman Coulter, Fullerton, CA). Results are analyzed by the Summit program (Beckman Coulter). Data analysis is conducted for SAPs after flow cytometry using the Summit program to determine the relative percentages of each of these groups per sample. The SAPs are expressed as a percentage of the total number of events in the sample.

Example 2: SAP Inhibition by Combinatorial Drug Treatment

Isolation and flow cytometry of SAPs was performed according to the procedure described in Example 1, above.

Aliquots of platelet rich plasma (PRP) were incubated with aqueous saline solutions of resveratrol only, quercetin only, naltrexone only, and with an admixture of resveratrol, quercetin and curcumin for a time period of 30 minutes at 37° C. Thereafter the obtained PRP samples were irradiated by an argon laser at 635 nm. Multi-color immunofluorescence was noted, and analyzed as described in Example 1, above. The obtained results are shown in Table 5, below. These data have been normalized relative to the Control (platelets incubated with thrombin and convulxin for five minutes).

TABLE 5

SAP Inactivation

| | % SAPs | % Reduction in SAPs |
|---|---|---|
| Control | 100 | 0 |
| Resveratrol (R), 10 μM | 53.4 | 46.6 |
| Quercetin (Q), 10 μM | 22.2 | 77.8 |
| Naltrexone (N), 50 μM | 47.8 | 52.2 |
| Resveratrol (10 μM), Quercetin (10 μM) and Naltrexone (50 μM) | 6.4 | 93.6 |

Dose Determination

RQC in triple combinations is synergistic at all dose levels evaluated including all combinations of each component at low, medium, and high doses (27 possible combinations). The dose that exhibits the highest degree of synergy on average in Alzheimer's disease subjects (n=9) is 1 μM R, 1 μM Q, and 0.01 μM C, corresponding to a highly synergistic combination index (CI) score of 0.25. The ratio of components at this dose is 10:10:1 (R:Q:C). The optimal in vivo dose therefore corresponds to an available dose (i.e., plasma concentration) of 1 μM R, 1 μM Q, and 0.01 μM C. After accounting for the bioavailability properties of each component, an in vivo dose of 1 μM R corresponds to about 200 mg consumed, 1 μM Q corresponds to about 240 mg consumed, and 0.1 μM C corresponds to about 2000 mg consumed (Table 6, below).

For curcumin, which has a relatively low bioavailability as compared to resveratrol and quercetin, we estimate that two capsules (1000 mg each) will achieve a maximum plasma concentration of about 0.6-1.0 μM. This dose will be taken twice daily to account for the low half-life of curcumin. The expected plasma availability of various doses is summarized in Table 6.

The desired in vivo dose equates to the in vitro dose with the highest level of synergy in the SAP inhibition assay. The in vitro dose with the highest average level of synergy was 1 μM R, 1 μM Q, and 0.01 μM C. After accounting for bioavailability, the given doses of 200 mg R, 240 mg Q, and 2000 mg C per day correspond to approximately 1 μM R, 1 μM Q, and 0.1 μM C, respectively.

TABLE 6

Determination of In Vivo Micromolar Dose Ranges Based on Milligram Concentrations

| Compound | Molar Mass (g/mol) | Bioavailability | Half-life | mg Range | | | | |
|---|---|---|---|---|---|---|---|---|
| Resveratrol (1) | 228.25 | 0.1-0.4% | 2-5 hr | 2 mg 0.01 μM | 20 mg 0.1 μM | 200 mg 1 μM (4) | 2,000 mg 10 μM | 10,000 mg 50 μM |
| Quercetin (2) | 302.24 | 0.2-0.3% | 3-17 hr | 2.4 mg 0.01 μM | 24 mg 0.1 μM | 240 mg 1 μM (4) | 2,400 mg 10 μM | 12,000 mg 50 μM |
| Curcumin (3) | 368.38 | 0.01-0.1% | 5-6 hr | 2 mg 0.0001 μM | 20 mg 0.001 μM | 200 mg 0.01 μM | 2,000 mg 0.1 μM (4) | 10,000 mg 1 μM |

TABLE 6 shows micromolar dose ranges for Resveratrol, Quercetin, and Curcumin based on milligram quantities and an estimation of the bioavailability of each compound. (1) Resveratrol micromolar doses range from 0.01 μM to 50 μM corresponding to 2 mg to 10,000 mg. The optimal plasma concentration of resveratrol is 1 μM corresponding to a daily dose quantity of 200 mg. (2) Quercetin micromolar doses range from 0.01 μM to 50 μM corresponding to 2.4 mg to 12,000 mg. The optimal plasma concentration of quercetin is 1 μM corresponding to a daily dose quantity of 240 mg. (3) Curcumin micromolar doses range from 0.001 μM to 1 μM corresponding to 2 mg to 10,000 mg. The optimal plasma concentration of curcumin is 1 μM corresponding to a daily dose quantity of 2000 mg. (4) The optimal micromolar dose for each compound is based on the in vitro dose with the highest synergy in the SAP inhibition assay. This dose was determined to be 1 μM resveratrol, 1 μM quercetin, and 0.1 μM curcumin.

Example 3: Nailfold Capillary Abnormalities in Alzheimer's Disease

Subjects with Alzheimer's disease routinely exhibit systemic microvascular capillary abnormalities that can be viewed and quantitated using nailfold capillaroscopy, a technique commonly used in the identification and diagnosis of certain rheumatic diseases. Nailfold capillary abnormalities have been measured in over 1000 people, including 20 people with Alzheimer's disease diagnosed by positron emission tomography (PET) imaging. In this analysis, included were eligible subjects with Alzheimer's disease (n=20) and all Caucasian controls over 65 years old who did not have any ocular or neurological conditions or diseases (n=46). The abnormalities measured included hemorrhages, dilated capillaries, avascular zones (capillary drop-out), and tortuosity (twisting or distortion of capillaries).

The total number of hemorrhages, dilated capillaries, and avascular zones were counted on two different fingers per subject, summed, and adjusted to counts per 100 capillaries. Hemorrhages were extravascular, bright-red to brown in color, and ranged from 50-200 μm in diameter. Dilated capillaries were defined as capillaries with a diameter≥50 μm. Avascular zones were defined as regions≥200 μm in diameter without capillaries. Tortuosity was assessed using a semi-quantitative scale from 0 to 3, with 0 being normal and 3 being severe tortuosity. Normal capillaries have no sinuous or crossing limbs (score of 0). Mildly tortuous capillaries (score of 1) have two sinuous limbs that cross over each other no more than once per capillary loop. Moderately tortuous capillaries (score of 2) have two highly sinuous limbs that cross over each other more than once. Severely tortuous capillaries (score of 3) have a total loss of hairpin architecture due to extreme sinuosity and limb cross-over.

In addition to evaluating the mean number of abnormalities, the proportion of subjects with "high" levels of each measure (i.e. 2 or more hemorrhages per 100 capillaries, 1 or more dilated capillaries per 100, 1 or more avascular zone per 100 capillaries, or tortuosity score 1.5 or higher, etc.) were compared between controls and subjects with Alzheimer's disease (Table 7, below).

Subjects with Alzheimer's disease had significantly increased hemorrhages and tortuosity relative to controls (Table 7). Alzheimer's disease subjects had a mean of 2.34 nailfold hemorrhages per 100 capillaries compared with only 0.74 in controls (p=0.0008). Only 7% of control subjects had 2 or more hemorrhages per 100 capillaries compared with 50% of the Alzheimer's disease subjects (p=0.0001). Tortuosity was also significantly increased in Alzheimer's disease compared with controls (1.59 vs. 0.89, p<0.0001). Likewise, a significantly higher proportion of Alzheimer's subjects had severe tortuosity scores (p=0.02). Dilated capillaries and avascular zones trended higher in Alzheimer's disease than in control subjects but the differences were not significant.

To examine nailfold capillary abnormalities in more detail, a parallel analysis was done exclusively in Alzheimer's disease subjects separated into three groups based on hemorrhage severity, i.e., number of hemorrhages. The groups consisted of "low" (0-1), "medium" (1-2), or "high" (2 or more) number of hemorrhages per 100 capillaries (Table 8). In this analysis, hemorrhage number was significantly associated with the number of dilated capillaries (p=0.04) but not avascular zones or tortuosity score. Hemorrhage number was also mildly associated with both sex and cognitive impairment as assessed by the Mini Mental State Examination (MMSE). Notably, Alzheimer's subjects with less than 1 hemorrhage had significantly higher (better) MMSE scores compared with those who had 1 or more hemorrhage (27.0 vs. 22.8, p=0.03), suggesting a possible relationship between the severity of systemic microvascular abnormalities and Alzheimer's disease progression.

TABLE 7

Cross-Sectional Analysis of Nailfold Capillary Abnormalities in Subjects with Alzheimer's Disease (AD) Compared with Aged Healthy Controls

| | Outcome | Control (n = 46) | AD (n = 20) | P-Value* |
|---|---|---|---|---|
| Demographics | Age | 71.61 | 77.80 | 0.007 |
| | Female, n (%) | 39% | 35% | 0.52 |
| | Caucasian, n (%) | 46 (100%) | 20 (100%) | 1.00 |
| Hemorrhages | Mean per 100 capillaries (SD) | 0.74 (0.9) | 2.34 (1.9) | 0.0008 |
| | ≥2, n (%) | 3 (7%) | 10 (50%) | 0.0001 |
| Dilated Capillaries | Mean per 100 capillaries (SD) | 0.61 (0.9) | 0.88 (1.1) | 0.15 |
| | ≥1, n (%) | 15 (33%) | 7 (35%) | 0.85 |
| Avascular Zones | Mean per 100 capillaries (SD) | 0.27 (0.5) | 0.41 (0.7) | 0.17 |
| | ≥1, n (%) | 3 (7%) | 4 (20%) | 0.10 |
| Tortuosity | Mean score (SD) | 0.89 (0.6) | 1.59 (0.6) | <0.0001 |
| | Score ≥1.5, n (%) | 8 (17%) | 9 (45%) | 0.02 |

AD, Alzheimer's disease.

*Significance determined by ANOVA for continuous data and Chi-square tests for categorical data. Statistical comparison is made between control and AD subjects.

TABLE 8

Cross-Sectional Analysis of Nailfold Capillary Abnormalities in Subjects with Alzheimer's Disease (AD) Stratified by Hemorrhage Severity

| Outcome | Low* Hemorrhages (0-1) | Medium* Hemorrhages (1-2) | P-Value† | High* Hemorrhages (≥2) | P-Value‡ |
|---|---|---|---|---|---|
| N (% of AD subjects) | 5 (25%) | 8 (40%) | — | 7 (35%) | — |
| Age, mean (SD) | 78.6 (7.4) | 80.6 (4.4) | 0.57 | 76.1 (11.8) | 0.69 |
| Female, n (%) | 1 (20%) | 1 (13%) | 0.72 | 5 (71%) | 0.08 |
| MMSE Score, mean (SD) | 25.3 (3.1) | 22.3 (6.1) | 0.43 | 23.8 (2.9) | 0.50 |
| Hemorrhages/100 Capillaries, mean (SD) | 0.71 (0.4) | 1.59 (0.3) | 0.0003 | 4.37 (1.9) | 0.001 |
| ≥2 Hemorrhages, n (%) | 0 (0%) | 3 (38%) | N/A | 7 (100%) | N/A |
| Dilated Capillaries/100 Capillaries, mean (SD) | 0.14 (0.3) | 0.99 (1.0) | 0.05 | 1.30 (1.3) | 0.04 |
| ≥1 Dilated Capillary, n (%) | 0 (0%) | 3 (38%) | N/A | 4 (57%) | N/A |
| Avascular Zones/100 Capillaries, mean (SD) | 0.40 (0.5) | 0.37 (0.5) | 0.47 | 0.47 (0.9) | 0.44 |
| ≥1 Avascular Zone, n (%) | 1 (20%) | 1 (13%) | 0.72 | 2 (29%) | 0.73 |
| Tortuosity Score 0-3, mean (SD) | 1.45 (0.5) | 1.78 (0.5) | 0.12 | 1.46 (0.8) | 0.49 |
| ≥1.5 Tortuosity Score, n (%) | 1 (20%) | 5 (63%) | 0.13 | 3 (43%) | 0.41 |

*Low hemorrhages: ≥0 and <1.0 hemorrhages/100 capillaries; Medium hemorrhages: ≥1.0 and <2.0 hemorrhages/100 capillaries; High hemorrhages: ≥2.0 hemorrhages/100 capillaries.

†Comparison between the Low and Medium Hemorrhage groups;

‡Comparison between the Low and High Hemorrhage groups.

Significance for all comparisons was determined using ANOVA for continuous data and chi-square tests for categorical data.

Hemorrhages were extravascular, bright-red to brown in color, and ranged from about 50-200 μm in diameter.

Dilated capillaries were defined as capillaries with a diameter ≥50 μm.

Avascular zones were defined as regions ≥200 μm in diameter without capillaries.

Tortuosity was assessed using a semi-quantitative scale from 0 to 3, with 0 being normal and 3 being severe tortuosity.

AD, Alzheimer's disease;

MMSE, Mini Mental State Examination;

SD, standard deviation.

Example 4: RQC Reduces Nailfold Hemorrhages in Alzheimer's Disease

Hemorrhages were tracked in three subjects with Alzheimer's disease before and after taking oral RQC (Table 9, below). In two subjects recorded over at least 16 months, hemorrhages per 100 capillaries decreased from 2.17 to 0.94 (−57%) and 6.8 to 3.7 (−46%), respectively. On a shorter timeframe, hemorrhages per 100 capillaries decreased from 1.8 to 0 (−100%) in one subject taking RQC for 3 months. Evaluating the effect of RQC in the combined group using data from baseline and the last available follow-up yielded a significance of P=0.021. Thus, oral RQC was statistically associated with reduced nailfold hemorrhages over a period between 1 and 16 months.

Another way to evaluate hemorrhages longitudinally is to classify hemorrhages as "old" or "fresh" based on appearance. Old hemorrhages are characterized by a dark brownish-red color and amorphous, diffused shape in contrast to fresh hemorrhages which are typically bright red in color and spherical or droplet-shaped. This technique accounts for noise introduced by hemorrhages that were previously counted but have not disappeared. This phenomenon can cause the appearance of an increasing number of hemorrhages despite a reduced incidence and can be clearly observed in Subject #2 after 1 month as shown in Table 9. Thus, to quantitate the change in hemorrhages, the number of fresh hemorrhages since baseline was analyzed. No fresh hemorrhages were observed after 3 months of treatment in one subject (−100%). Another subject had 10 fresh hemorrhages at baseline, 9 fresh hemorrhages after 1 month (−61%), and 0 fresh hemorrhages by 16 months (−100%). The final subject had 1 fresh hemorrhages at baseline and 0 at 3 months (−100%). Thus, the number of fresh, incident hemorrhage was decreased from baseline to final follow-up in all subjects. A detailed view of each subject included in the overall nailfold analysis is given in Table 10.

TABLE 9

Longitudinal Analysis of Nailfold Hemorrhages in Three Subjects with Alzheimer's Disease (AD) Taking Oral RQC

| Subject # | Age | Sex | Race | Follow-Up (months) | Number of Hems* | Hems/100 Capillaries † | Old‡ Hems (brown) | Fresh‡ Hems (red) |
|---|---|---|---|---|---|---|---|---|
| 1 | 79 | Male | Caucasian | 0.0 | 5 | 2.174 | 1 | 4 |
| | | | | 3.0 | 4 | 1.961 | 4 | 0 |
| | | | | 10.3 | 2 | 1.227 | 1 | 1 |
| | | | | 16.3 | 2 | 0.943 | 1 | 1 |
| 2 | 59 | Female | Caucasian | 0.0 | 15 | 6.818 | 5 | 10 |
| | | | | 0.9 | 26 | 13.613 | 17 | 9 |
| | | | | 16.8 | 6 | 3.704 | 6 | 0 |

TABLE 9-continued

Longitudinal Analysis of Nailfold Hemorrhages in Three Subjects with Alzheimer's Disease (AD) Taking Oral RQC

| Subject # | Age | Sex | Race | Follow-Up (months) | Number of Hems* | Hems/100 Capillaries † | Old‡ Hems (brown) | Fresh‡ Hems (red) |
|---|---|---|---|---|---|---|---|---|
| 3 | 89 | Male | Caucasian | 0.0 | 2 | 1.770 | 1 | 1 |
| | | | | 3.1 | 0 | 0.000 | 0 | 0 |

*Hems, hemorrhages.

† The number of hemorrhages was adjusted to counts per 100 capillaries.

‡Old hemorrhages are characterized by a dark brownish-red color and amorphous, diffused shape. Fresh hemorrhages are typically bright red in color and spherical or droplet shaped.

TABLE 10

Detailed demographic and outcome data for all control and Alzheimer's disease subjects evaluated in the cross-sectional nailfold analysis

| Site ID | Subject Type | Age | Race | Sex | Hemorrhages/100 Capillaries | Dilated Capillaries/100 | Avascular Zones/100 Capillaries | Mean Tortuosity Score |
|---|---|---|---|---|---|---|---|---|
| 35 | Control | 66 | W | F | 1.587 | 0 | 0 | 1.50 |
| 41 | Control | 67 | W | M | 0 | 0 | 0 | 0.80 |
| 59 | Control | 71 | W | F | 1.053 | 0 | 0 | 1.00 |
| 86 | Control | 70 | W | F | 0.5 | 0 | 0 | 0.00 |
| 90 | Control | 78 | W | F | 0 | 2.577 | 0 | 0.60 |
| 95 | Control | 74 | W | F | 0 | 0 | 0 | 1.50 |
| 96 | Control | 64 | W | M | 0.893 | 0 | 0 | 1.67 |
| 118 | Control | 88 | W | F | 0.714 | 0 | 0 | 0.25 |
| 120 | Control | 66 | W | M | 0 | 1.307 | 0 | 0.40 |
| 121 | Control | 81 | W | M | 1.449 | 0 | 1.450 | 2.00 |
| 123 | Control | 68 | W | F | 0.935 | 0 | 0 | 1.00 |
| 131 | Control | 75 | W | M | 1.818 | 0 | 0 | 0.75 |
| 132 | Control | 63 | W | M | 0.741 | 2.222 | 1.481 | 1.50 |
| 135 | Control | 66 | W | F | 0 | 0.694 | 0 | 0.50 |
| 136 | Control | 65 | W | F | 0.752 | 0 | 0.752 | 0.75 |
| 149 | Control | 70 | W | M | 0.730 | 0 | 0 | 0.75 |
| 153 | Control | 72 | W | M | 1.840 | 0.613 | 0.613 | 0.75 |
| 157 | Control | 64 | W | F | 0 | 0 | 0 | 1.75 |
| 161 | Control | 73 | W | M | 0.676 | 2.027 | 0 | 0.50 |
| 167 | Control | 61 | W | F | 0 | 2.941 | 0 | 0.00 |
| 172 | Control | 83 | W | F | 3.636 | 0.000 | 0 | 1.25 |
| 179 | Control | 75 | W | M | 0.746 | 2.985 | 0 | 1.33 |
| 184 | Control | 73 | W | F | 0.769 | 0 | 0 | 0.00 |
| 185 | Control | 78 | W | M | 0 | 0 | 1.639 | 1.00 |
| 186 | Control | 71 | W | F | 0 | 0 | 0 | 1.75 |
| 189 | Control | 70 | W | M | 0 | 0.813 | 0 | 0.50 |
| 192 | Control | 62 | W | F | 0.820 | 0 | 0.820 | 0.25 |
| 199 | Control | 66 | W | M | 0.775 | 0.775 | 0 | 0.25 |
| 202 | Control | 88 | W | M | 0.833 | 1.667 | 1.667 | 0.25 |
| 205 | Control | 77 | W | F | 0 | 0 | 0 | 0.33 |
| 216 | Control | 80 | W | F | 0.917 | 0.917 | 0.917 | 0.50 |
| 220 | Control | 67 | W | F | 0.000 | 0 | 0 | 1.67 |
| 225 | Control | 67 | W | F | 2.439 | 1.220 | 1.220 | 1.67 |
| 247 | Control | 65 | W | M | 0.556 | 0 | 0 | 1.00 |
| 250 | Control | 70 | W | F | 0 | 0 | 0 | 1.25 |
| 258 | Control | 68 | W | F | 0 | 0 | 0.476 | 1.00 |
| 266 | Control | 88 | W | M | 0.621 | 0 | 0 | 0.60 |
| 267 | Control | 82 | W | M | 3.049 | 1.829 | 0.610 | 1.00 |
| 269 | Control | 70 | W | F | 1.961 | 0 | 0 | 2.00 |
| 282 | Control | 67 | W | F | 0 | 1.887 | 0 | 0.00 |
| 290 | Control | 80 | W | M | 1.923 | 1.923 | 0.641 | 1.00 |
| 302 | Control | 74 | W | F | 0.662 | 0 | 0 | 1.25 |
| 307 | Control | 61 | W | F | 0 | 0.714 | 0 | 0.00 |
| 309 | Control | 61 | W | F | 0 | 0.971 | 0 | 1.75 |
| 315 | Control | 71 | W | F | 0 | 0.000 | 0 | 0.00 |
| 330 | Control | 78 | W | F | 0.738 | 0 | 0 | 1.50 |
| 177 | AD | 69 | W | M | 0 | 0 | 0 | 1.00 |
| 212 | AD | 84 | W | F | 5.882 | 0 | 0 | 2.50 |
| 218 | AD | 85 | W | F | 0.893 | 0 | 0 | 1.00 |
| 264 | AD | 71 | W | F | 3.279 | 3.279 | 0 | 2.25 |
| 268 | AD | 74 | W | M | 5.952 | 2.381 | 2.381 | 0.50 |
| 283 | AD | 80 | W | M | 1.205 | 3.012 | 0.602 | 1.25 |
| 284 | AD | 87 | W | M | 0.676 | 0.676 | 0 | 2.00 |
| 285 | AD | 85 | W | 1 | 2.400 | 1.600 | 0 | 2.00 |
| 292 | AD | 77 | W | M | 1.099 | 0 | 1.11 | 1.75 |
| 310 | AD | 93 | W | F | 2.083 | 0 | 0 | 1.00 |
| 319 | AD | 81 | W | F | 1.563 | 0 | 0 | 2.00 |
| 327 | AD | 82 | W | M | 1.408 | 0 | 0 | 2.00 |
| 303 | AD | 59 | W | F | 6.818 | 1.818 | 0.909 | 1.25 |
| 151 | AD | 80 | W | M | 1.794 | 0 | 0 | 2.00 |
| 380 | AD | 66 | W | M | 1.626 | 1.626 | 0 | 1.50 |
| 381 | AD | 75 | W | M | 0.870 | 0 | 0.870 | 1.50 |
| 382 | AD | 67 | W | M | 4.162 | 0 | 0 | 0.75 |
| 383 | AD | 77 | W | M | 1.389 | 1.389 | 1.389 | 1.00 |
| 384 | AD | 89 | W | M | 1.942 | 0.971 | 0.971 | 2.00 |
| 385 | AD | 75 | W | M | 1.818 | 0.909 | 0 | 2.50 |

AD, Alzheimer's disease;
F, female;
M, male;
W, white race.

Example 5: Superactivated Platelets are Increased in Alzheimer's Disease

Superactivated platelets (SAPs), also called coated platelets in the literature, are a pro-coagulant sub-type of activated platelets that act as platforms for thrombin generation at sites of vessel injury. In vivo, SAPs are formed by dual activation with the classical platelet agonist thrombin and extracellular matrix component collagen exposed by vessel injury. Thus, abnormally high SAP levels are indicative of microvascular disease. In vitro, SAPs are induced using thrombin plus convulxin—a collagen substitute. SAPs are characterized by their spherical shape, high levels of phosphatidylserine exposure, high fibrinogen binding, and inactivated integrin GPIIbIIIa. Activated platelets and SAPs are identified using flow cytometry to detect the presence of fluorophore-labeled antibodies. Operationally, SAPs are defined as platelets negative for activated integrin GPIIbIIIa and positive for surface fibrinogen. In healthy controls, SAPs make up around 36% of platelets on average. In certain diseases and conditions associated with microvascular injury, however, SAP % can be significantly higher with averages in the range of 50-60%. We thus evaluated whether subjects with Alzheimer's disease had a higher percentage of SAPs leading to platelet aggregation relative to controls.

SAPs were measured after activation with thrombin and convulxin in 25 healthy control subjects and 14 Alzheimer's disease subjects. The mean age of controls (73.3±7.7) was not significantly different from that of Alzheimer's disease subjects (77.8±8.5, p=0.06). The mean SAP level in control subjects was 36.4% (±SD 5.4%, n=24). In Alzheimer's disease subjects, SAP levels were on average significantly higher than in healthy controls (48.8%±5.7%, p<0.0001). See Table 11, below. Moreover, SAP levels were significantly higher in Alzheimer's disease than other degenerative diseases including age-related macular degeneration (AMD, p=0.03). To analyze Alzheimer's disease subjects with varying SAP levels, Alzheimer's disease (AD) subjects were divided into tertiles (i.e., three groups) based on SAP %: AD-High SAPs represent those with SAPs in the 66th to 100th percentile. AD-Medium SAPs represent those with SAPs in the 33rd to 66th percentile. AD-Low SAPs represent those with SAPs in the 0 to 33rd percentile. Alzheimer's disease subjects with the lowest SAP levels had a significantly a higher SAP % compared with controls (p=0.03).

TABLE 11

Percentage of Untreated Superactivated Platelets (SAPs) in Subjects with Alzheimer's Disease (AD) compared with Healthy Controls and Subjects with Age-Related Macular Degeneration (AMD)

| Group | N | SAP % (Untreated) | SD | P value vs. Control † | P value vs. AMD ‡ |
|---|---|---|---|---|---|
| AD | 14 | 48.8% | 5.7% | <0.0001 | 0.02 |
| AD (High SAPs*) | 5 | 55.4% | 2.5% | <0.0001 | <0.0001 |
| AD (Medium SAPs*) | 5 | 47.3% | 1.5% | 0.0002 | 0.21 |
| AD (Low SAPs*) | 4 | 42.5% | 0.8% | 0.03 | 0.37 |
| Control (normal) | 24 | 36.4% | 5.4% | Reference | <0.0001 |
| AMD | 18 | 44.6% | 4.5% | <0.0001 | Reference |

*AD subjects were divided into tertiles based on SAP %: high SAPs represent those with SAPs in the 66th to 100th percentile; medium SAPs represent those with SAPs in the 33rd to 66th percentile, low SAPs represent those with SAPs in the 0 to 33rd percentile.
† P-value compared with control subjects.
‡ P-value compared with AMD subjects.
Significance for all comparisons was determined using ANOVA.
AD, Alzheimer's disease;
AMD, age-related macular degeneration;
SAPs, superactivated platelets.

Example 6: Synergistic Inhibition of Superactivated Platelets with RQC

To evaluate the effect of RQC on SAP formation, SAPs were induced and measured in vitro in nine AD subjects with and without RQC at high, medium, and low doses (Table 12). "Low dose" RQC means 1 μM R, 1 μM Q, and 0.01 μM C; "medium dose" RQC means 5 μM R, 5 μM Q, and 0.1 μM C; and "high dose" RQC means 10 μM R, 10 μM Q, and 1 μM C. At each of the low, medium, and high doses (P<0.0001), RQC significantly inhibits SAPs in Alzheimer's disease subjects.

To evaluate synergistic drug effects, the Combination Index (CI) theorem derived by Chou-Talalay was calculated for each combination product of R, Q, and C. The CI is useful in quantifying levels of synergism and antagonism. The theorem is based on the median-effect equation to provide a common link between a single entity and multiple entities. A CI value<1 indicates synergism, a CI equal to 1 indicates additivity, and a CI>1 indicates antagonism. RQC exhibits significant synergy at the high dose (mean CI=0.42), medium dose (mean CI=0.41), and low dose (mean CI=0.25). The synergy of RQC ranged from 0.014 to 1.87 in Alzheimer's disease subjects. Notably, RQC acts as a synergistic drug in Alzheimer's disease subjects in addition to AMD subjects.

To evaluate whether the triple combination of RQC is synergistic, high dose of RQC was compared to double combinations of RQ, RC, or QC (Table 13). High doses of RQ, RC, and CQ each significantly inhibited SAPs, however RQ, RC, or CQ exhibited no synergy in Alzheimer's disease subjects. For example, the high doses of RQ, RC, and QC exhibit mean CI scores of 2.31, 2.57, and 2.09, respectively. Compared with any combination of RQ, RC, or CQ, the triple combination of RQC exhibited a significantly lower mean combination index (P<0.0001). The CI scores for the low, medium, and high doses of RQ, RC, CQ, and RQC are shown in Table 14, below. In general, there was an association between lower synergy scores and lower doses for all double and triple combinations. RQC is significantly more synergistic than RQ, RC, and QC at the low, medium, and high dose levels. These results indicate a significant difference between double and triple combinations of RQC in Alzheimer's disease subjects, with only the triple combination exhibiting synergistic inhibition of SAPs. Therefore, the combination of RQC is synergistic, i.e., more effective than the sum of its parts.

To examine whether the synergy observed in RQC is associated with SAP levels, synergy was evaluated in nine Alzheimer's disease subjects grouped by SAP % into tertiles consisting of low, medium, or high SAPs (Table 15 and Table 16. below). RQC in low, medium, and high doses all exhibited a CI score<1, i.e., synergism, in all three SAP level groups.

TABLE 12

Synergy Analysis Showing the Effect of RQC in Low, Medium, and High Triple Combinations on the Percentage of Superactivated Platelets (SAPs) in Alzheimer's Disease (AD) Subjects (n = 9)

| | Untreated | RQC (Low Dose) | RQC (Medium Dose) | RQC (High Dose) |
|---|---|---|---|---|
| Mean SAP % ± SD | 48.6 ± 5.8% | 34.5 ± 3.7% | 31.6 ± 4.3% | 28.1 ± 3.4% |
| % Change ± SD | — | −28.5 ± 8.5% | −34.6 ± 8.3% | −41.7 ± 7.5% |
| P value* | — | 0.00004 | 0.000007 | 0.000002 |
| Combination Index ± SD | — | 0.25 ± 0.24 | 0.41 ± 0.29 | 0.42 ± 0.36 |

All subjects included had Alzheimer's disease (n = 9).
"Low Dose" RQC 1 μM R, 1 μM Q, and 0.01 μM C;
"Medium Dose" RQC 5 μM R, 5 μM Q, and 0.1 μM C; and
"High Dose" RQC 10 μM R, 10 μM Q, and 1 μM C.
*Two-tailed paired t-test comparing RQC-treated samples with untreated samples

TABLE 13

Comparison of RQ, RC, and QC with RQC in Alzheimer's disease (AD) Subjects (n = 9) In Vitro

| | RQC (High Dose) | RQ (High Dose) | RC (High Dose) | CQ (High Dose) |
|---|---|---|---|---|
| % Change ± SD | −42.2 ± 7.3% | −30.8 ± 11.7% | −27.6 ± 11.1% | −27.4 ± 9.7% |
| P value* | Reference | 0.0408 | 0.0132 | 0.0067 |
| Combination Index ± SD | 0.42 ± 0.37 | 2.31 ± 2.07 | 2.57 ± 2.04 | 2.09 ± 1.72 |
| P value□ | — | 0.0158 | 0.0067 | 0.0111 |

*Two-tailed paired t-test evaluating % change against RQC (High);
□Two-tailed t-test evaluating the combination index of RQ, RC, and CQ in high doses against RQC (High).
RQ (High) 10 μM R and 10 μM Q;
RC (High) 10 μM R and 1 μM C;
CQ (High) 1 μM C and 10 μM Q;
RQC (High) 10 μM R, 10 μM Q, and 1 μM C.

TABLE 14

Synergy Analysis Comparing the Effect of Double Combinations of RQ, RC, and QC with the Full Triple Combination RQC on the Percentage of Superactivated Platelets (SAPs) in Alzheimer's disease (AD) Subjects (n = 9) In Vitro

| | RQC | RQ | RC | CQ |
|---|---|---|---|---|
| CI ± SD (Low Dose) | 0.25 ± 0.24 | 1.87 ± 2.94 | 1.43 ± 1.22 | 2.28 ± 1.93 |
| CI ± SD (Med. Dose) | 0.41 ± 0.29 | 2.19 ± 3.05 | 1.83 ± 1.94 | 2.02 ± 0.99 |
| CI ± SD (High Dose) | 0.42 ± 0.36 | 2.31 ± 2.07 | 2.57 ± 2.04 | 2.09 ± 1.72 |

CI, combination index.
"Low doses" 1 μM R, 1 μM Q, and/or 0.01 μM C;
"medium doses" 5 μM R, 5 μM Q, and/or 0.1 μM C;
"high doses" 10 μM R, 10 μM Q, and/or 1 μM C.

TABLE 15

Synergy Analysis in AD Subjects (n = 9) Divided into Tertiles Based on Baseline SAP Levels

| Tertiles | n | SAP % | RQC Low Dose Mean CI | RQC Medium Dose Mean CI | RQC High Dose Mean CI |
|---|---|---|---|---|---|
| High SAPs (top tertile) | 3 | 54.8% | 0.14 | 0.48 | 0.67 |
| Medium SAPs (middle tertile) | 3 | 48.2% | 0.15 | 0.55 | 0.34 |
| Low SAPs (bottom tertile) | 3 | 42.3% | 0.46 | 0.19 | 0.25 |

CI, combination index;
SAPs, superactivated platelets.
"Low dose" RQC 1 μM R, 1 μM Q, and 0.01 μM C;
"medium dose" RQC 5 μM R, 5 μM Q, and 0.1 μM C; and
"high dose" RQC 10 μM R, 10 μM Q, and 1 μM C.

Baseline differences in untreated SAP levels can be adjusted for by evaluating the proportion of total platelets that are sensitive or resistant to treatment (Table 16). This technique adjusts for overall differences in SAP levels between various disease types. Sensitive platelets are defined as the proportion of total platelets inhibited from becoming SAPs using RQC. Resistant platelets are defined as the proportion of total platelets unaffected by RQC, i.e., platelets that become SAPs even after treatment with RQC. Sensitive SAPs are defined as the percentage of SAPs inhibited by RQC. In AD subjects (n=9), the total number of platelets sensitive to RQC was higher than in healthy controls (n=20). Conversely, the total number of SAPs that are sensitive to RQC is increased in healthy controls compared with AD. The number of sensitive platelets was higher in AD subjects with higher SAP levels while the number of resistant platelets remained largely equivalent. Two complete examples of synergistic inhibition of SAPs using RQC are shown in Table 17 and Table 18.

TABLE 16

RQC Dose Effect In Vitro on SAPs in AD Subjects

| | SAP % [1] | Sensitive Platelets [2] | Resistant Platelets [3] | Sensitive SAPS [4] | P Value [5] |
|---|---|---|---|---|---|
| AD: All (n = 9) [6] | | | | | |
| High dose | 48.6% | 20.4% | 28.1% | 42.1% | 0.0001 |
| Medium dose | 48.6% | 16.5% | 32.0% | 34.0% | 0.0002 |
| Low dose | 48.6% | 13.6% | 35.0% | 28.0% | 0.002 |
| AD: High SAPs (n = 3) [7] | | | | | |
| High dose | 55.2% | 25.3% | 29.9% | 45.8% | 0.003 |
| Medium dose | 55.2% | 20.6% | 34.6% | 37.4% | 0.004 |
| Low dose | 55.2% | 18.4% | 36.8% | 33.4% | 0.02 |
| AD: Medium SAPs (n = 3) [7] | | | | | |
| High dose | 48.2% | 19.9% | 28.3% | 41.2% | 0.007 |
| Medium dose | 48.2% | 14.7% | 33.4% | 30.6% | 0.006 |
| Low dose | 48.2% | 10.9% | 37.3% | 22.6% | 0.01 |
| AD: Low SAPs (n = 3) [7] | | | | | |
| High dose | 42.3% | 16.1% | 26.2% | 38.1% | 0.03 |
| Medium dose | 42.3% | 14.2% | 28.1% | 33.6% | 0.07 |
| Low dose | 42.3% | 11.4% | 30.9% | 27.0% | 0.01 |

Key:
AD, Alzheimer's disease;
SAPs, superactivated platelets.
[1] SAPs are defined as the percentage of total platelets positive for surface fibrinogen binding and negative for activated integrin αIIbβ3 after activation with thrombin and convulxin.
[2] Sensitive platelets are defined as the number of platelets inhibited from becoming SAPs with RQC.
[3] Resistant platelets are defined as the number of platelets unaffected by RQC, i.e., platelets that become SAPs even after treatment with RQC.
[4] Sensitive SAPs are defined as the percentage of SAPs inhibited by RQC.
[5] Significance was determined by two-way ANOVA comparing the proportion of sensitive to resistant platelets in each group with healthy controls.
[6] All AD subjects evaluated with RQC regardless of SAP level.
[7] AD subjects were divided into tertiles (i.e., three groups) based on SAP %: AD-High SAPs represent those with SAPs in the $66^{th}$ to $100^{th}$ percentile. AD-Medium SAPs represent those with SAPs in the $33^{rd}$ to $66^{th}$ percentile. AD-Low SAPs represent those with SAPs in the 0 to $33^{rd}$ percentile.

TABLE 17

Example of RQC Synergy in a Control Subject
Example of Synergy Analysis
Control Patient
71 Year Old Caucasian Male

| R (μM) | Q (μM) | C (μM) | SAP % | % Change | Combination Index |
|---|---|---|---|---|---|
| — | — | — | 37.2% | — | — |
| 1 | — | — | 33.9% | −9% | — |
| 5 | — | — | 28.2% | −24% | — |
| 10 | — | — | 26.3% | −29% | — |
| — | 1 | — | 34.2% | −8% | — |
| — | 5 | — | 32.5% | −13% | — |
| — | 10 | — | 28.6% | −23% | — |
| — | — | 0.01 | 36.6% | −2% | — |
| — | — | 0.1 | 34.6% | −7% | — |
| — | — | 1 | 32.9% | −12% | — |

TABLE 17-continued

| Example of RQC Synergy in a Control Subject<br>Example of Synergy Analysis<br>Control Patient<br>71 Year Old Caucasian Male | | | | | |
|---|---|---|---|---|---|
| R (μM) | Q (μM) | C (μM) | SAP % | % Change | Combination Index |
| 1 | — | 0.01 | 30.4% | −18% | 0.25 |
| 5 | — | 0.01 | 27.6% | −26% | 0.30 |
| 10 | — | 0.01 | 29.2% | −21% | 0.33 |
| 1 | — | 0.1 | 24.3% | −35% | 0.10 |
| 5 | — | 0.1 | 22.6% | −39% | 0.11 |
| 10 | — | 0.1 | 28.7% | −23% | 1.22 |
| 1 | — | 1 | 23.1% | −38% | 0.51 |
| 5 | — | 1 | 22.4% | −40% | 0.54 |
| 10 | — | 1 | 20.9% | −44% | 0.33 |
| — | 1 | 0.01 | 26.2% | −30% | 0.04 |
| — | 5 | 0.01 | 24.9% | −33% | 0.13 |
| — | 10 | 0.01 | 23.2% | −38% | 0.21 |
| — | 1 | 0.1 | 28.4% | −24% | 0.46 |
| — | 5 | 0.1 | 24.3% | −35% | 0.21 |
| — | 10 | 0.1 | 22.1% | −41% | 0.21 |
| — | 1 | 1 | 25.6% | −31% | 1.26 |
| — | 5 | 1 | 21.7% | −42% | 0.38 |
| — | 10 | 1 | 19.6% | −47% | 0.27 |
| 1 | 1 | — | 34.3% | −8% | 1.11 |
| 5 | 5 | — | 32.4% | −13% | 1.61 |
| 10 | 10 | — | 31.7% | −15% | 2.30 |
| 1 | 1 | — | 33.9% | −9% | 1.43 |
| 5 | 5 | — | 32.1% | −14% | 1.73 |
| 10 | 10 | — | 30.4% | −18% | 1.62 |
| 1 | 1 | — | 29.8% | −20% | 0.92 |
| 5 | 5 | — | 30.3% | −19% | 1.20 |
| 10 | 10 | — | 28.9% | −22% | 1.23 |
| 1 | 1 | 0.01 | 12.5% | −66% | 0.01 |
| 1 | 5 | 0.01 | 15.3% | −59% | 0.04 |
| 1 | 10 | 0.01 | 14.3% | −62% | 0.07 |
| 5 | 1 | 0.01 | 16.3% | −56% | 0.03 |
| 5 | 5 | 0.01 | 15.0% | −60% | 0.05 |
| 5 | 10 | 0.01 | 15.2% | −59% | 0.09 |
| 10 | 1 | 0.01 | 14.1% | −62% | 0.03 |
| 10 | 5 | 0.01 | 15.7% | −58% | 0.08 |
| 10 | 10 | 0.01 | 15.9% | −57% | 0.12 |
| 1 | 1 | 0.1 | 15.0% | −60% | 0.01 |
| 1 | 5 | 0.1 | 15.7% | −58% | 0.05 |
| 1 | 10 | 0.1 | 17.4% | −53% | 0.11 |
| 5 | 1 | 0.1 | 14.8% | −60% | 0.02 |
| 5 | 5 | 0.1 | 13.3% | −64% | 0.04 |
| 5 | 10 | 0.1 | 14.8% | −60% | 0.09 |
| 10 | 1 | 0.1 | 14.6% | −61% | 0.04 |
| 10 | 5 | 0.1 | 15.7% | −58% | 0.08 |
| 10 | 10 | 0.1 | 17.6% | −53% | 0.16 |
| 1 | 1 | 1 | 16.7% | −55% | 0.07 |
| 1 | 5 | 1 | 17.1% | −54% | 0.08 |
| 1 | 10 | 1 | 15.9% | −57% | 0.13 |
| 5 | 1 | 1 | 16.7% | −55% | 0.08 |
| 5 | 5 | 1 | 15.0% | −60% | 0.08 |
| 5 | 10 | 1 | 16.8% | −55% | 0.17 |
| 10 | 1 | 1 | 14.5% | −61% | 0.06 |
| 10 | 5 | 1 | 18.4% | −51% | 0.21 |
| 10 | 10 | 1 | 16.2% | −56% | 0.17 |

TABLE 18

| Example of RQC Synergy in Subject with Alzheimer's Disease<br>Example of Synergy Analysis<br>Alzheimer's Disease Patient<br>80 Year Old Caucasian Male | | | | | |
|---|---|---|---|---|---|
| R (μM) | Q (μM) | C (μM) | SAP % | % Change | Combination Index |
| — | — | — | 36.8% | — | — |
| 1 | — | — | 33.6% | −9% | — |
| 5 | — | — | 30.5% | −17% | — |
| 10 | — | — | 29.9% | −19% | — |

TABLE 18-continued

Example of RQC Synergy in Subject with Alzheimer's Disease
Example of Synergy Analysis
Alzheimer's Disease Patient
80 Year Old Caucasian Male

| R (μM) | Q (μM) | C (μM) | SAP % | % Change | Combination Index |
|---|---|---|---|---|---|
| — | 1 | — | 34.3% | −7% | — |
| — | 5 | — | 26.7% | −27% | — |
| — | 10 | — | 20.6% | −44% | — |
| — | — | 0.01 | 32.5% | −11% | — |
| — | — | 0.1 | 30.0% | −18% | — |
| — | — | 1 | 23.2% | −37% | — |
| 1 | — | 0.01 | 15.3% | −58% | 0.04 |
| 5 | — | 0.01 | 27.6% | −25% | 1.10 |
| 10 | — | 0.01 | 23.1% | −37% | 1.12 |
| 1 | — | 0.1 | 15.6% | −58% | 0.04 |
| 5 | — | 0.1 | 15.2% | −59% | 0.20 |
| 10 | — | 0.1 | 28.4% | −23% | 2.56 |
| 1 | — | 1 | 23.8% | −35% | 0.14 |
| 5 | — | 1 | 14.1% | −62% | 0.17 |
| 10 | — | 1 | 22.0% | −40% | 0.97 |
| — | 1 | 0.01 | 30.6% | −17% | 1.14 |
| — | 5 | 0.01 | 23.3% | −37% | 1.12 |
| — | 10 | 0.01 | 33.8% | −8% | 1.09 |
| — | 1 | 0.1 | 29.7% | −19% | 0.47 |
| — | 5 | 0.1 | 26.1% | −56% | 0.93 |
| — | 10 | 0.1 | 30.7% | −17% | 1.27 |
| — | 1 | 1 | 29.2% | −37% | 1.81 |
| — | 5 | 1 | 25.9% | −30% | 0.68 |
| — | 10 | 1 | 28.1% | −24% | 2.39 |
| 1 | 1 | — | 28.0% | −24% | 0.43 |
| 5 | 5 | — | 31.2% | −15% | 0.22 |
| 10 | 10 | — | 30.5% | −17% | 1.00 |
| 1 | 1 | — | 19.0% | −48% | 2.75 |
| 5 | 5 | — | 27.2% | −26% | 1.85 |
| 10 | 10 | — | 28.6% | −22% | 1.42 |
| 1 | 1 | — | 24.3% | −34% | 4.26 |
| 5 | 5 | — | 23.9% | −35% | 3.73 |
| 10 | 10 | — | 25.6% | −30% | 2.74 |
| 1 | 1 | 0.01 | 25.0% | −32% | 0.25 |
| 1 | 5 | 0.01 | 20.8% | −43% | 0.31 |
| 1 | 10 | 0.01 | 23.7% | −36% | 0.88 |
| 5 | 1 | 0.01 | 25.3% | −31% | 0.87 |
| 5 | 5 | 0.01 | 27.1% | −26% | 0.83 |
| 5 | 10 | 0.01 | 29.6% | −19% | 0.96 |
| 10 | 1 | 0.01 | 28.2% | −23% | 0.94 |
| 10 | 5 | 0.01 | 27.1% | −26% | 0.57 |
| 10 | 10 | 0.01 | 26.1% | −29% | 0.90 |
| 1 | 1 | 0.1 | 22.5% | −39% | 0.17 |
| 1 | 5 | 0.1 | 25.9% | −29% | 0.76 |
| 1 | 10 | 0.1 | 24.3% | −34% | 0.98 |
| 5 | 1 | 0.1 | 21.8% | −41% | 0.52 |
| 5 | 5 | 0.1 | 23.8% | −35% | 0.92 |
| 5 | 10 | 0.1 | 24.2% | −34% | 0.88 |
| 10 | 1 | 0.1 | 25.1% | −32% | 0.91 |
| 10 | 5 | 0.1 | 24.5% | −33% | 0.92 |
| 10 | 10 | 0.1 | 20.7% | −44% | 0.72 |
| 1 | 1 | 1 | 21.4% | −42% | 0.14 |
| 1 | 5 | 1 | 22.5% | −39% | 0.42 |
| 1 | 10 | 1 | 21.7% | −41% | 0.62 |
| 5 | 1 | 1 | 24.9% | −32% | 0.86 |
| 5 | 5 | 1 | 22.6% | −39% | 0.84 |
| 5 | 10 | 1 | 19.6% | −47% | 0.71 |
| 10 | 1 | 1 | 21.0% | −43% | 0.89 |
| 10 | 5 | 1 | 17.2% | −53% | 0.64 |
| 10 | 10 | 1 | 17.0% | −60% | 0.79 |

Example 7. RQC Dose Determination Based on Synergy Score

RQC is a synergistic three-drug combination at all dose levels evaluated including all combinations of each component at low, medium, and high doses (27 possible combinations). The desired in vivo dose of RQC equates to the in vitro dose with the highest level of synergy with respect to inhibition of SAPs. The dose that exhibits the highest degree of synergy on average in Alzheimer's disease subjects (n=9) is 1 μM R, 1 μM Q, and 0.1 μM C, corresponding to a highly synergistic combination index (CI) score of 0.25. The mol ratio of components at this dose is 10:10:1 (R:Q:C).

The optimal in vivo dose therefore corresponds to an available dose (i.e., plasma concentration) of 1 μM R, 1 μM Q, and 0.1 μM C. After accounting for the bioavailability properties of each component, an in vivo dose of 1 μM R corresponds to about 200 mg consumed, 1 μM Q corresponds to about 240 mg consumed, and 0.1 μM C corresponds to about 2000 mg consumed. For curcumin, which has a low bioavailability relative to resveratrol and quercetin, we estimate that two capsules (1000 mg each) will achieve a maximum plasma concentration of about 0.6-1.0 μM. This dose will be taken twice daily to account for the low half-life of curcumin. The expected plasma availability of various doses is summarized in Table 19.

TABLE 19

Determination of In Vivo Micromolar Dose Ranges Based on Milligram Concentrations

| Compound | Molar Mass (g/mol) | Bioavailability | Half-life | mg Range | | | | |
|---|---|---|---|---|---|---|---|---|
| Resveratrol (1) | 228.25 | 0.1-0.4% | 2-5 hr | 2 mg 0.01 μM | 20 mg 0.1 μM | 200 mg 1 μM (4) | 2,000 mg 10 μM | 10,000 mg 50 μM |
| Quercetin (2) | 302.24 | 0.2-0.3% | 3-17 hr | 2.4 mg 0.01 μM | 24 mg 0.1 μM | 240 mg 1 μM (4) | 2,400 mg 10 μM | 10,000 mg 50 μM |
| Curcumin (3) | 368.38 | 0.01-0.1% | 5-6 hr | 2 mg 0.0001 μM | 20 mg 0.001 μM | 200 mg 0.01 μM | 2,000 mg 0.1 μM (4) | 10,000 mg 1 μM |

Micromolar (μM) dose ranges for R, Q, and C based on milligram quantities and an estimation of the bioavailability of each compound. (1) Resveratrol micromolar doses range from 0.01 μM to 50 μM corresponding to 2 mg to 10,000 mg with an optimal dose of 1 μM corresponding to a quantity of 200 mg. (2) Quercetin micromolar doses range from 0.01 μM to 50 μM corresponding to 2.4 mg to 10,000 mg with an optimal dose of 1 μM corresponding to a quantity of 240 mg. (3) Curcumin micromolar doses range from 0.0001 μM to 1 μM corresponding to 2 mg to 10,000 mg with an optimal dose of 0.1 μM corresponding to a quantity of 2000 mg. (4) The optimal micromolar dose for each compound based on the in vitro dose with the highest synergy. The possible micromolar concentration for RQC as single entity/drug ranges from 0.01 to 50 μM for resveratrol, 0.01 to 50 μM for quercetin, and 0.0001 to 1 μM for curcumin. As a single entity (RQC) the possible micromolar concentration ranges from 0.0201 to 101 μM not accounting for synergistic metabolic interactions.

Example 8: In Vivo Analysis of SAPs in Subjects Taking Oral RQC

Figure 10:
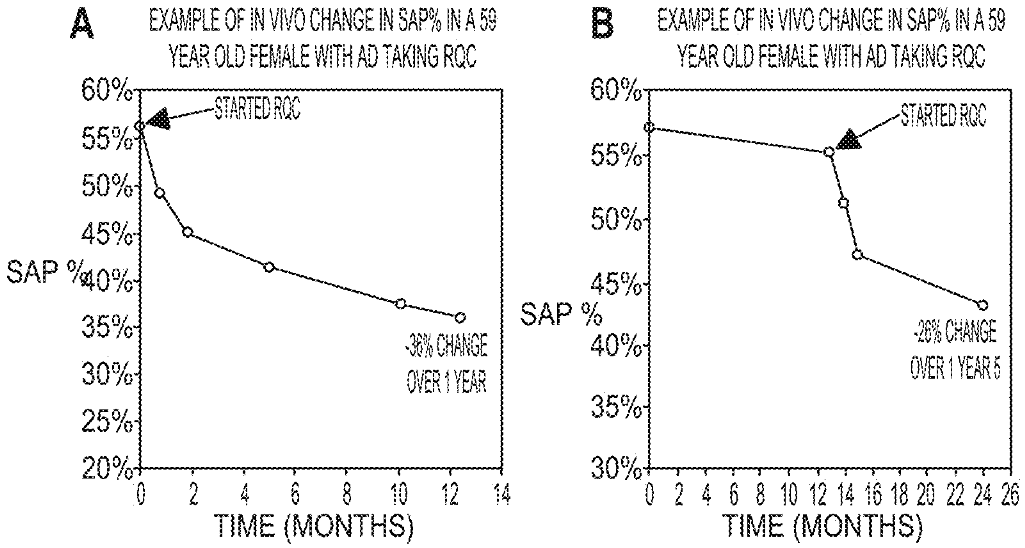
FIG. 10 shows superactivated platelets (SAPs) percentage over one year in two subjects with Alzheimer's disease taking oral RQC. (A) Subject is a 78-year old male with mild cognitive impairment confirmed to be sporadic early Alzheimer's disease through PET imaging. The percentage of SAPs in this subject decreased by 39% from 56.3% at baseline to 34.3%. (B) Subject is a 59-year old female with mild cognitive impairment confirmed to have Alzheimer's disease through PET imaging. This subject likely had a familial, or genetic, form of Alzheimer's disease based on family history and the severity of conditions given the subject's age. The percentage of SAPs in this subject decreased 29% over two years of treatment.

In subjects with Alzheimer's disease taking oral RQC, SAPs were measured longitudinally at repeated intervals over at least two years (n=2, FIG. 10). In these subjects, SAPs were consistently decreased by 6 months and remained decreased over the rest of the two-year period. In one subject, SAPs were reduced from 56% to 34%, representing a percentage change of −39% over two years. This reduction altered the SAP score in this subject from abnormally high (but typical for Alzheimer's disease) to around the average SAP value for control subjects. In the other subject, SAPs were reduced from 57% to 44%, a change of −29% over 2 years.

Example 9: Identification of Retinal Beta-Amyloid Using Curcumin

The eye is an extension of the brain and is the only CNS tissue unobstructed from view. As part of the CNS, the retina contains many of the same cell types and undergoes many of the same physiological and pathophysiological processes as the brain. It has long been evident that manifestations of Alzheimer's disease can be seen in the eye. In fact, ophthalmologic studies of AD have found significant ocular changes associated with Alzheimer's disease.

Figure 11:
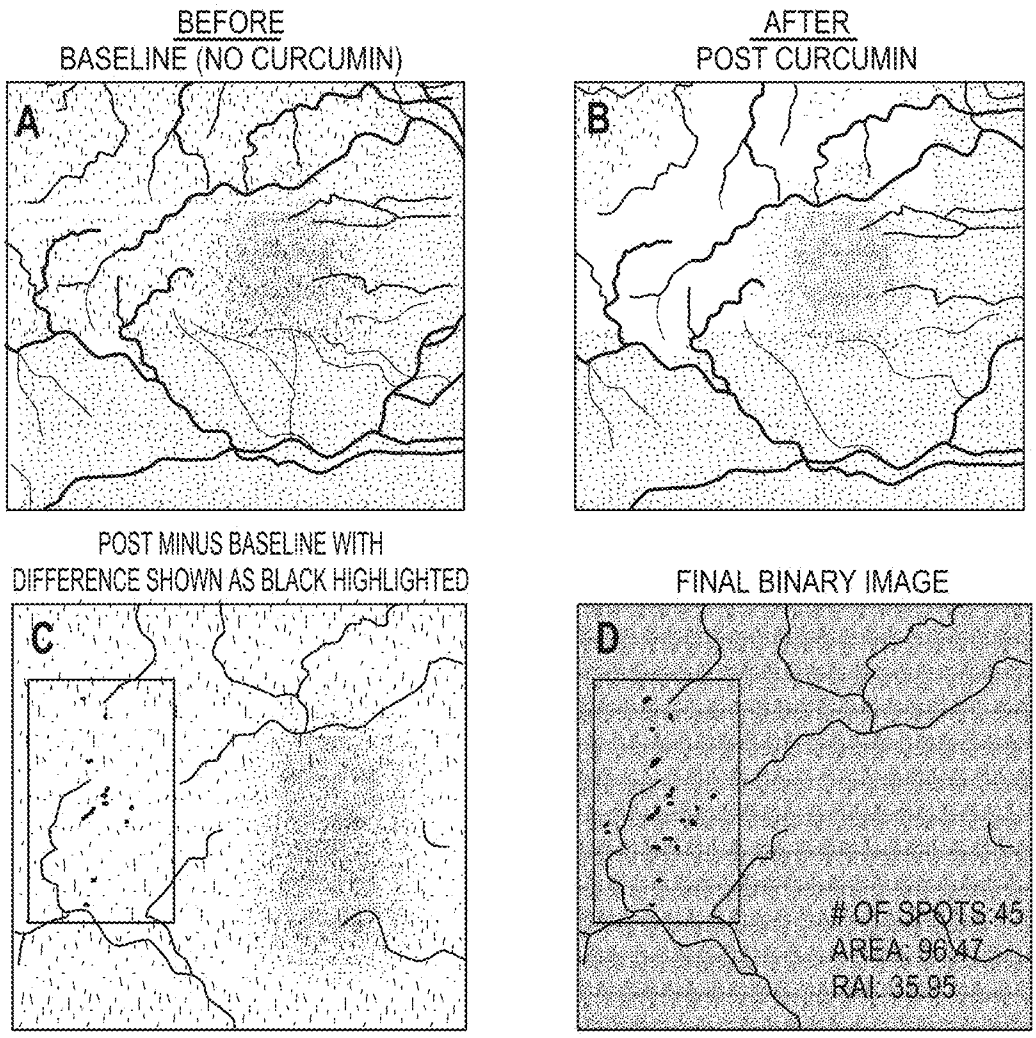
FIG. 11 shows an example of the method used to identify retinal beta-amyloid in a patient with Alzheimer's disease. Briefly, (A) baseline images are acquired using the Heidelberg Spectralis-BAF module before the patient consumes concentrated curcumin. (B) Imaging is repeated after 2-10 days taking oral curcumin. (C) After post processing the images, differences in hyperfluorescence are identified and then segmented. The thresholded area represents areas of increased fluorescence at $\lambda$=488 nm. A final binary image shows only the isolated retinal beta-amyloid (D). Note the presence of hyperfluorescence in areas called "hot spots" depicting 45 spots, an area of 96.47, and a retinal amyloid index (RAI) of 35.95.
Figure 12:
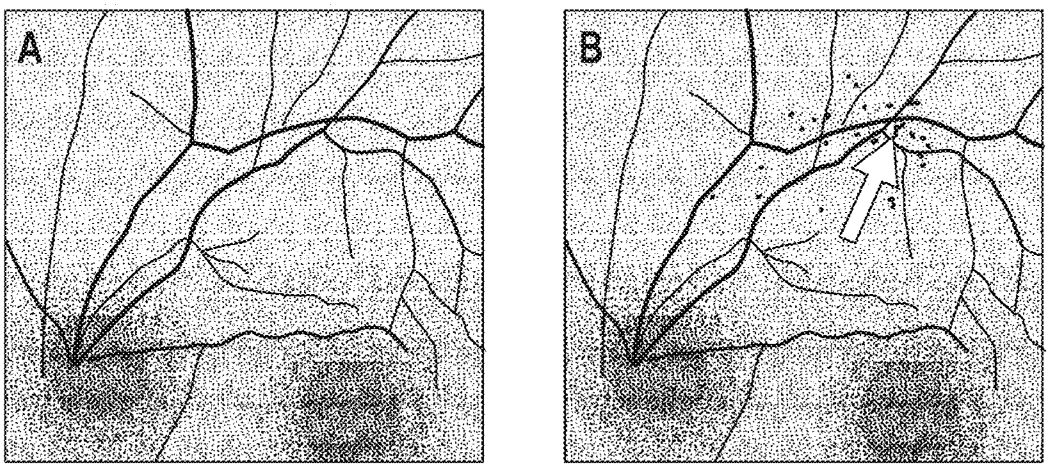
FIG. 12 shows an example of curcumin-labeled retinal beta-amyloid identified in a patient with Alzheimer's disease. Panel (A) on the left is the pre-curcumin baseline image. Panel (B) on the right is the final processed image showing the identified spots of retinal beta-amyloid as dark spots (hot spots) highlighted by the arrow. Note the characteristic localization of retinal beta-amyloid in the superior retina with clustering around blood vessels.

Recently, it has become possible to quantitate retinal beta-amyloid in vivo in living subjects using fundus blue-light autofluorescence (FAF) photography and curcumin as a contrast agent. Imaging can be performed on most conventional ocular coherence tomography (OCT) systems with autofluorescence capabilities (FIG. 11). Curcumin has intrinsic fluorescence properties and binds to beta-amyloid fibrils and oligomers with high affinity and specificity. The ability to track beta-amyloid in CNS tissue in vivo opens the door to clinical trials using retinal beta-amyloid as an endpoint. This method is significantly cheaper, more accessible, and less dangerous than those currently used to identify beta-amyloid in clinical trials, namely positron emission tomography (PET) imaging and spinal tap procedures to obtain cerebrospinal fluid samples. Our laboratory has successfully detected retinal beta-amyloid using curcumin, an example of which is shown in FIG. 11.

The procedure to identify retinal beta-amyloid using the FAF-curcumin method is given in detail below:

1. Subjects are imaged using the Heidelberg Spectralis OCT Blue-Peak Autofluorescence (BAF) module (Heidelberg Engineering Inc., Franklin, MA) before starting curcumin in order to acquire a pre-curcumin baseline image. Multiple BAF images are recorded from each eye to increase image quality.
2. Subjects then take oral curcumin (1000 mg twice per day) for 2-10 days before a second imaging session.
3. Subjects are imaged a second time using the Heidelberg Spectralis OCT BAF module after starting curcumin (Step 2) in order to acquire a post-curcumin experimental image. The BAF fundus images are then extracted from the Heidelberg Eye Explorer Software as Tag Image File Format (TIFF) files.
4. Image processing may be performed manually using ImageJ software or automatically using proprietary programs such as Afina® Retinal Autofluorescence Measurement Software (NeuroVision Imaging, Inc., Sacramento, CA). For manual measurements, images obtained from the same eye are merged to create a higher-resolution image. The pre-curcumin baseline image and post-curcumin experimental image are then stacked onto one another and adjusted to match alignment, brightness, and contrast. Confounding structural features such as blood vessels are masked. Edge detection is performed to further contrast hyperfluorescent spots from the background. The curcumin fluorescence intensity (λ=488 nm) is identified as the difference between pixel intensity levels in the baseline and post-curcumin images. The remaining thresholded areas are then analyzed in terms of number of individual spots, area ($mm^2$), and fluorescence intensity.

5. The retinal amyloid index (RAI) score is calculated combining the spot number, area, and fluorescence intensity in order to quantitate the overall beta-amyloid load.

Example 10: Retinal Beta-Amyloid is Increased in Alzheimer's Disease

Retinal beta-amyloid accumulates during aging and can be seen in all adult subjects. However, the extent of beta-amyloid deposition specifically distinguishes Alzheimer's disease (AD) from control subjects, other types of dementias (e.g., vascular dementia, frontotemporal dementia, etc.), and other types of age-related degenerative diseases. To evaluate retinal beta-amyloid in AD, OCT was performed using the Heidelberg Spectralis BluePeak Autofluorescence module. Subjects were imaged at the baseline visit. After 1 week of taking oral RQC, subjects returned and were imaged again. All AD subjects had independent diagnoses based on cognitive testing and PET imaging.

Figure 13:
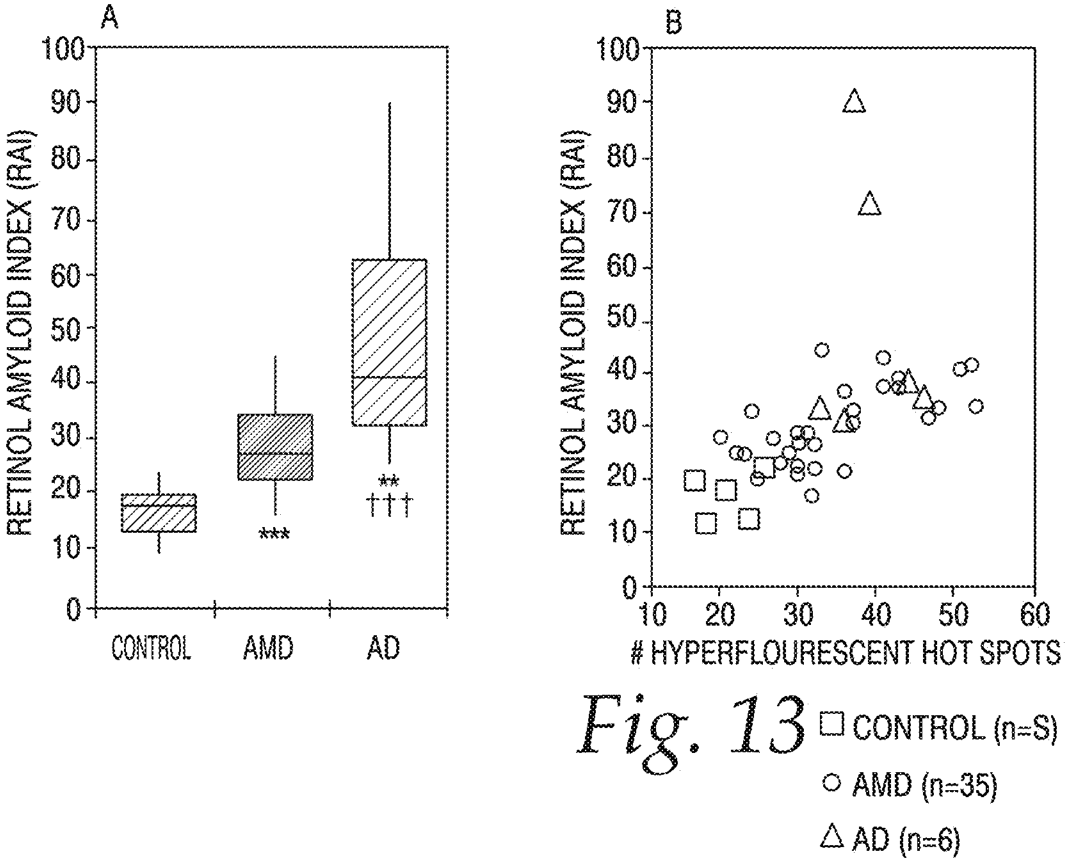
FIG. 13 shows the distribution of retinal beta-amyloid in healthy controls, subjects with Alzheimer's disease (AD), and age-related macular degeneration (AMD). (A) Whisker plots of the retinal amyloid index (RAI) score in healthy control subjects, age-related macular degeneration (AMD), and Alzheimer's disease (AD). Statistical significance was determined by two-way ANOVA. $P<0.01$ compared with controls, *$P<0.001$ compared with controls, ††$P<0.0001$ compared with AMD. (B) Dot plot showing the retinal amyloid index (RAI) versus the number of fluorescent spots in control (squares), AD (triangles), and AMD (circles) subjects. Control subjects have low RAI scores and low numbers of spots relative to other groups. Alzheimer's disease subjects have very high RAI scores and high numbers of spots. AMD, age-related macular degeneration.

As shown in Table 20 and FIG. 13, the retinal amyloid index (RAI) was significantly increased in AD subjects compared with both controls (P=0.006) and subjects with age-related macular degeneration (AMD; P<0.0001). Individual components of the RAI including the number of discrete spots and particularly the total spot area were also increased in AD subjects. Table 21 shows the individual RAI data for each AD and control subject.

TABLE 20

Cross-Sectional Analysis of Retinal Beta-Amyloid Hot Spots Measured in Control Subjects and Patients with Alzheimer's Disease (AD)

| | N | Discrete Spot # (SD) | Area (SD) $mm^2$ | RAI* (SD) | P Value □ |
|---|---|---|---|---|---|
| Control | 5 | 20.2 (3.8) | 36.9 (9.6) | 17.0 (4.5) | 0.006 |
| Alzheimer's disease | 6 | 38.2 (5.0) | 128.8 (106.7) | 52.4 (24.7) | Reference |

*Retinal amyloid index (RAI) scores incorporate the number of individual retinal amyloid spots, the total area of retinal amyloid, and the mean fluorescence intensity of identified amyloid spots. The score is calculated for each eye in individual. If both eyes of any subject were available for analysis, only the worse eye was considered here.
□ P values were calculated using two-way ANOVA comparing AD to other groups.
RAI, retinal amyloid index;
SD, standard deviation.

TABLE 21

Cross-Sectional Analysis of Retinal Beta-Amyloid Index (RAI) Scores in Individual Alzheimer's Disease (AD, n = 6) and Control Subjects (n = 5)

| Patient ID | Group | Age | Baseline Date | Retinal Amyloid Index (RAI)* |
|---|---|---|---|---|
| 001 | AD | 80 | May 10, 2018 | 76.48 |
| 002 | AD | 61 | Apr. 19, 2018 | 95.14 |
| 003 | AD | 67 | Oct. 15, 2018 | 28.99 |
| 004 | AD | 75 | Jan. 25, 2019 | 49.02 |
| 005 | AD | 89 | Apr. 11, 2019 | 38.93 |
| 006 | AD | 75 | Nov. 8, 2018 | 32.00 |
| 007 | Control | 53 | May 29, 2019 | 11.90 |
| 008 | Control | 74 | Aug. 13, 2020 | 22.40 |
| 009 | Control | 75 | Feb. 28, 2019 | 12.96 |
| 010 | Control | 71 | Jun. 5, 2019 | 19.75 |
| 011 | Control | 62 | Apr. 4, 2019 | 18.07 |

*Retinal amyloid index (RAI) scores incorporate the number of individual retinal amyloid spots, the total area of retinal amyloid, and the mean fluorescence intensity of identified amyloid spots. The score is calculated for each eye in individual. If both eyes of any subject were available for analysis, only the worse eye was considered.
All AD subjects had independent diagnoses based on cognitive testing and PET imaging.
AD, Alzheimer's disease.

Figure 14:
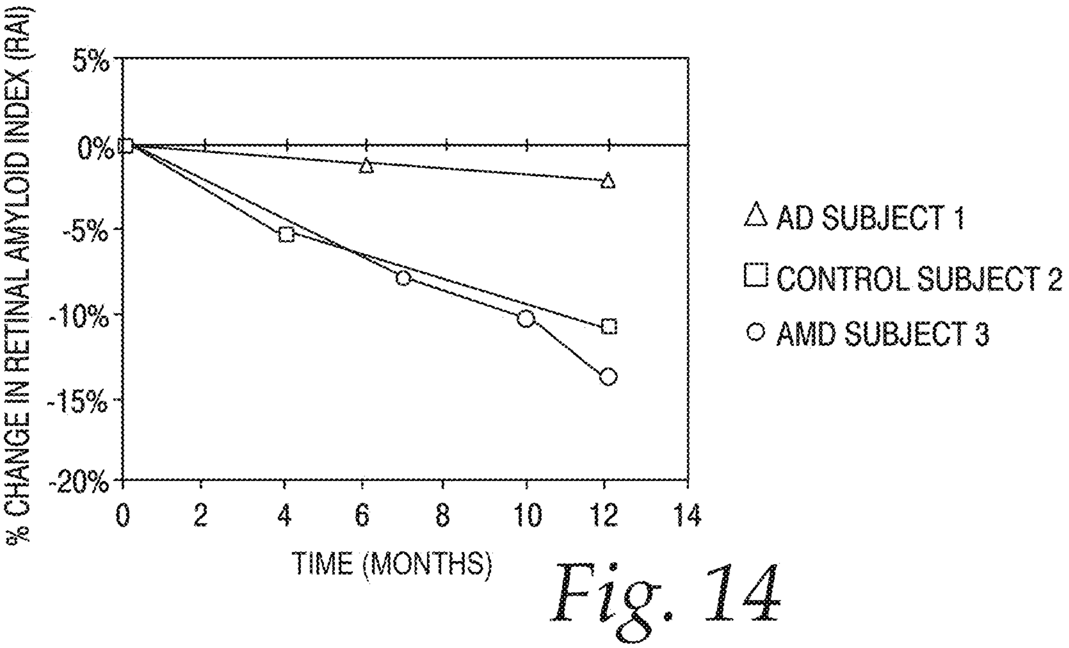
FIG. 14 shows a longitudinal analysis of retinal beta-amyloid index (RAI) scores in three subjects with Alzheimer's disease taking oral RQC over one year. The y-axis shows the percentage change in RAI score against time on the x-axis. After 1 year, RAI scores decreased in all three subjects (Subject 1: −2.3%, Subject 2: −10.8%, and Subject 3: −13.9%, $p=0.06$).
Figure 15:
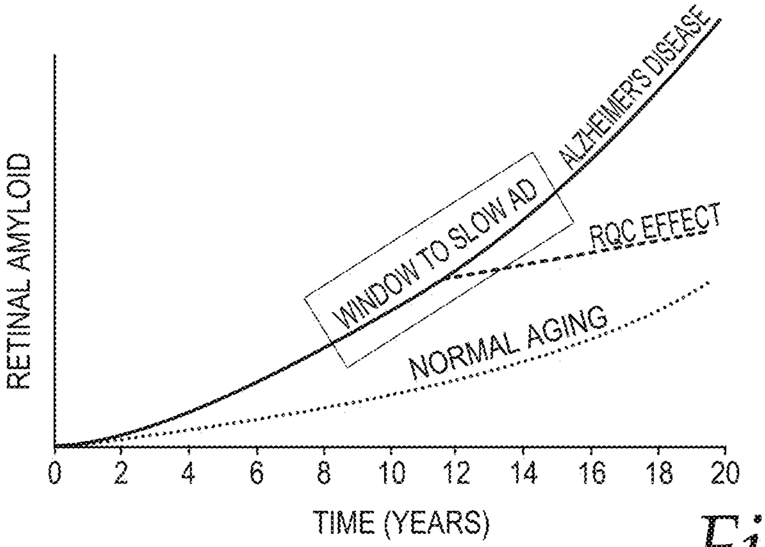
FIG. 15 shows the effect of RQC on retinal beta-amyloid levels over time. Retinal beta amyloid levels increase significantly over time in Alzheimer's disease compared with normal aging. Therapeutic intervention can prevent or slow the disease process with early intervention reducing retinal beta-amyloid. A critical treatment window exists between the identification of elevated retinal amyloid and irreversible damage resulting in Alzheimer's disease leading to dementia. Treatment with RQC during the treatment window could help to prevent or slow progression of the disease.

Example 11: Longitudinal Analysis of Retinal Beta-Amyloid Index (RAI) Scores in Alzheimer's Disease Taking Oral RQC To evaluate the effect of RQC on retinal beta-amyloid over time, retinal beta-amyloid index (RAT) scares were measured in three subjects with Alzheimer's disease (AD) taking oral RQC over one year (Table 22; FIG. 14). In all three subjects taking RQC, RAT scores decreased over one year (−2.3%, −10.8%, and −13.9%, respectively). Recent studies showing that beta-amyloid-induced cell death is decreased by the use of TLR4 inhibitors support the idea that RQC have multiple anti-beta-amyloid mechanisms. In untreated subjects, RAT scares are expected to increase slowly over time as a part of normal aging and rapidly in patients with AD as the disease worsens in severity (FIG. 15). Longitudinal use of the RAT score may be beneficial to the prevention of Alzheimer's disease.

TABLE 22

Longitudinal Analysis of Retinal Beta-Amyloid Index (RAI) Scores in Alzheimer's Disease (AD) Subjects Taking Oral ROC

| Patient ID | Group | Age | Baseline Date | Retinal Amyloid Index (RAI), Longitudinal Baseline | 3 Months | 6 Months | 12 months | % Change (12 months) |
|---|---|---|---|---|---|---|---|---|
| 001 | AD | 80 | May 10, 2018 | 76.48 | — | 72.54 | 68.22 | −10.8% |
| 002 | AD | 61 | Apr. 19, 2018 | 95.14 | — | 94.00 | 92.95 | −2.3% |
| 003 | AD | 67 | Oct. 15, 2018 | 28.99 | 29.54 | 29.82 | 24.97 | −13.9% |

Retinal amyloid index (RAI) scores incorporate the number of discrete spots, the total area of retinal amyloid, and the mean fluorescence intensity of identified amyloid spots. If both eyes of any subject were available for analysis, only the worse eye was analyzed. Baseline column shows the cross-sectional analysis, whereas columns titled 3 Months, 6 Months,and 12 Months show longitudinal data. AD, Alzheimer's disease.

Example 12. RQC De-Aggregates Beta-Amyloid

The formation of beta-amyloid plaques in the brain is a major hallmark of Alzheimer's disease and is widely considered to be a key initial step in the disease progression. The aim of clinical trials for Alzheimer's disease has historically been to deaggregate or prevent the aggregation of beta-amyloid. Plaques are formed by aggregation of soluble monomeric beta-amyloid into insoluble oligomers, protofibrils, fibrils, and plaques. The beta-amyloid (1-42) isoform more prevalent in the brain is more susceptible to aggregation than the (1-40) form more prevalent in the blood. The most common method to evaluate beta-amyloid aggregation is the thioflavin-T (ThT) assay. ThT is a fluorescent probe that binds to beta-amyloid fibrils with specificity and is measurable at 482 nm when excited at 450 nm.

Figure 16:
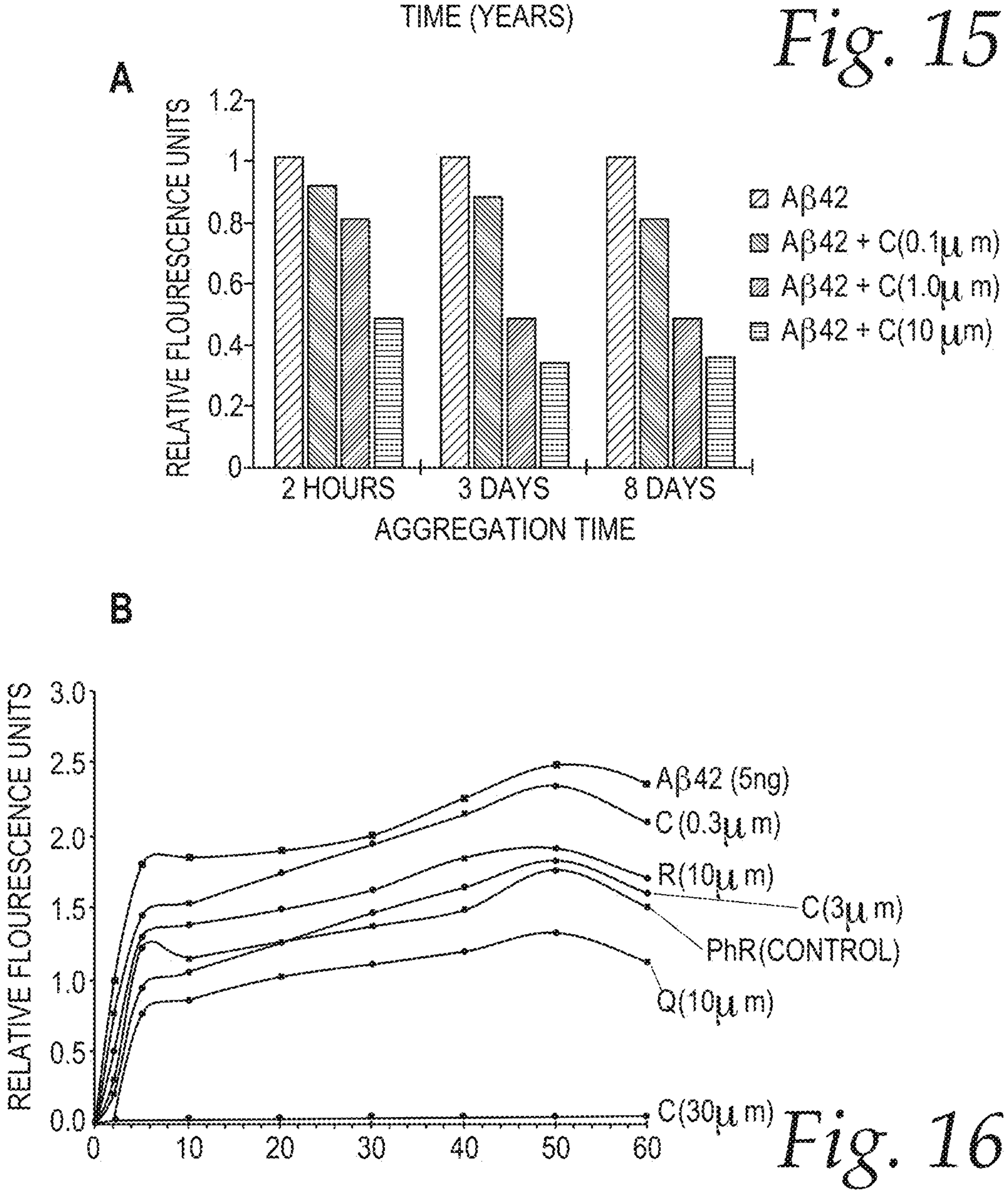
FIG. 16 shows the in vitro anti-beta-amyloid aggregation activity of RQC. (A) De-aggregation activity of curcumin (C). Monomeric beta-amyloid 1-42 (5 ng) was pre-aggregated into oligomeric form before incubation at 37° C. with and without curcumin (0.1, 1.0, or 10 μM) for 2 hours, 3 days, and 8 days. Curcumin de-aggregated beta-amyloid oligomers in a dose-dependent manner at all time points. (B) Aggregate-prevention activity of resveratrol (R), quercetin (Q), and curcumin (C). Monomeric beta-amyloid 1-42 (5 ng) was incubated with and without curcumin (C; 0.1, 1.0, or 10 μM), resveratrol (10 PM), quercetin (10 μM), or positive control phenol red (PhR) for 60 minutes. Curcumin, resveratrol and quercetin each inhibited the formation of new beta-amyloid aggregates. Curcumin again exhibited dose-dependent.

The ability of curcumin (C) to de-aggregate or prevent the aggregation of beta-amyloid (1-42) oligomers and fibrils was measured using the ThT assay (FIG. 16). Curcumin (C) was evaluated at 0.1, 1.0, and 10 μM. All tests were performed using 5 ng monomeric beta-amyloid (1-42) (Anaspec, Fremont, CA). As shown in Panel (A) of FIG. 16, curcumin dose-dependently de-aggregated existing beta-amyloid oligomers over 2 hours, 3 days, and 8 days. Curcumin at 0.1, 1.0, and 10 μM reduced aggregation over 8 days by about 18.6% ($p<0.05$), 51.8% ($p<0.05$), and 64.7% ($p<0.05$), respectively. As shown in Panel (B) of FIG. 16, curcumin, resveratrol, and quercetin each inhibited the formation of new beta-amyloid aggregates. Curcumin at 1 μM and resveratrol at 10 μM were approximately as effective as the positive control phenol red (PhR), which is known to inhibit beta-amyloid aggregation.

Example 13: Unit Dose Formulation

A uniform powder blend of RQN is formulated as a 10-gram batch for encapsulation or packaging in folded paper sachets using the amounts of active pharmaceutical ingredients (APIs) shown in Table 23, below.

TABLE 23

APIs in Exemplary Unit Doses

| Formulation | Dose (mg) | Batch (g) |
|---|---|---|
| Resveratrol | 2.28 | 1.14 |
| Quercetin | 1.37 | 0.685 |
| Naltrexone | 5.17 | 2.585 |
| Mannitol | 9.98 | 4.99 |
| Sucralose | 0.8 | 0.4 |
| Colloidal silica dioxide | 0.2 | 0.1 |
| Magnesium stearate | 0.2 | 0.1 |
| | 20 | 10 |

One unit dose equivalent of the resulting powder blend is then encapsulated using a tabletop capsule filling machine and hard gelatin or hydroxypropyl-methylcellulose (HPMC) capsules.

Example 14: Unit Dose Formulation

A uniform powder blend of RQC is formulated as a 10-gram batch for encapsulation or packaging in folded paper sachets using the amounts of active pharmaceutical ingredients (APIs) shown in Table 24, below.

TABLE 24

APIs in Exemplary Unit Doses

| Formulation | Dose (mg) | Batch (g) |
|---|---|---|
| Resveratrol | 0.72 | 0.36 |
| Quercetin | 0.87 | 0.43 |
| Curcumin | 7.23 | 3.61 |
| Mannitol | 9.98 | 5.00 |
| Sucralose | 0.8 | 0.4 |
| Colloidal silica dioxide | 0.2 | 0.1 |
| Magnesium stearate | 0.2 | 0.1 |
| | 20 | 10 |

One unit dose equivalent of the resulting powder blend is then encapsulated using a tabletop capsule filling machine and hard gelatin or hydroxypropyl-methylcellulose (HPMC) capsules.

The foregoing discussion and the examples are intended as illustrative and are not to be taken as limiting. Still other variants within the spirit and scope of the invention are possible and will readily present themselves to those skilled in the art.

REFERENCES

Chou T C. Drug combination studies and their synergy quantification using the Chou-Talalay method. Cancer Research. 2010; 70(2):440-446.

Dong et al., Angew. Chem. Int. Ed., 2014; 53: 9430-9448.

Mazepa et al., Arterioscler Thromb Vasc Biol 33:1747-1752 (2013).

The invention claimed is:

1. A method of treating a subject suffering from Alzheimer's Disease which comprises administering to the subject a synergistic amount of resveratrol, quercetin, and curcumin.

2. The method in accordance with claim 1 wherein daily administered amounts of resveratrol are in the range of about 200 milligrams to about 2,000 milligrams, of quercetin are in the range of about 240 milligrams to about 2,400 milligrams, and of curcumin are in the range of about 200 milligrams to about 10,000 milligrams.

3. The method in accordance with claim 2 wherein the daily administered amount of resveratrol is about 200 milligrams, of quercetin is about 240 milligrams, and of curcumin is about 2,000 milligrams.

4. The method in accordance with claim 2 wherein the daily administered amounts are administered in a single dose.

5. The method in accordance with claim 2 wherein the daily administered amounts are administered in multiple divided doses.

6. The method in accordance with claim 1 wherein the synergistic amount is sufficient to provide a subject's plasma concentration of resveratrol in a range of about 1 μM to about 10 μM, quercetin in a range of about 1 μM to about 10 μM, and curcumin in a range of about 0.01 μM to about 1 μM.

7. The method in accordance with claim 1 wherein the synergistic amount is sufficient to provide a subject's plasma concentration of resveratrol about 1 μM, quercetin about 1 μM, and curcumin about 0.1 μM.

* * * * *